United States Patent [19]
Galt et al.

[11] 4,268,514
[45] * May 19, 1981

[54] 1'-SUBSTITUTED XANTHENE-9-SPIRO-4'-PIPERIDINE DERIVATIVES AND ANALGESIC COMPOSITIONS THEREOF

[75] Inventors: Ronald H. B. Galt; Robert J. Pearce, both of Macclesfield, England

[73] Assignee: Imperial Chemical Industries Limited, London, England

[*] Notice: The portion of the term of this patent subsequent to Jan. 4, 1994, has been disclaimed.

[21] Appl. No.: 732,293

[22] Filed: Oct. 14, 1976

Related U.S. Application Data

[63] Continuation of Ser. No. 539,742, Jan. 9, 1975, Pat. No. 4,001,419.

[30] Foreign Application Priority Data

Feb. 4, 1974 [GB] United Kingdom ............... 5016/74

[51] Int. Cl.³ ............... A61K 31/445; C07D 491/107
[52] U.S. Cl. ................... 424/267; 260/335; 542/401; 546/17; 546/217
[58] Field of Search .................. 260/293.58; 424/267; 546/17; 542/401

[56] References Cited

U.S. PATENT DOCUMENTS 3,048,595  8/1962  Zirkle ........................ 260/293.4
3,652,558  3/1972  Lunsford et al. .......... 260/326.35 X Primary Examiner—Henry R. Jiles
Assistant Examiner—Richard A. Schwartz
Attorney, Agent, or Firm—Cushman, Darby & Cushman

[57] ABSTRACT

The disclosure relates to xanthene derivatives which possess analgesic activity, to processes for the manufacture of said derivatives and to pharmaceutical compositions containing them. Typical of the xanthene derivatives disclosed is 6-chloro-4-hydroxy-1'-methylxanthene-9-spiro-4'-piperidine.

3 Claims, No Drawings

1'-SUBSTITUTED XANTHENE-9-SPIRO-4'-PIPERIDINE DERIVATIVES AND ANALGESIC COMPOSITIONS THEREOF

This is a continuation, of application Ser. No. 539,742 filed Jan. 9, 1975, now U.S. Pat. No. 4,001,419.

This invention relates to xanthene derivatives which possess analgesic properties.

According to the invention there is provided a xanthene derivative of the formula:

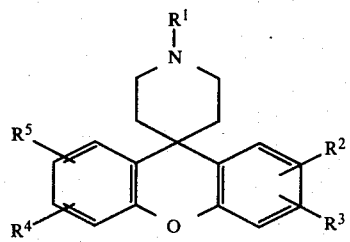

wherein
$R^1$ stands for
1. a hydrogen atom or an
2. alkyl radical of 1 to 10 carbon atoms;
3. an alkenyl radical of 3 to 10 carbon atoms;
4. a haloalkenyl radical of 3 to 6 carbon atoms;
5. an alkynyl radical of 3 to 6 carbon atoms;
6. a cycloalkylalkyl radical of 4 to 7 carbon atoms, optionally substituted in the cycloalkyl nucleus by an aryl radical of 6 to 10 carbon atoms or by one or two alkyl radicals of 1 to 3 carbon atoms;
7. a phenyl radical;
8. an arylalkyl radical of 7 to 10 carbon atoms, optionally substituted in the aryl nucleus by one to three halogen atoms or alkyl radicals of 1 to 3 carbon atoms;
9. an aroylalkyl radical of 8 to 12 carbon atoms, optionally substituted in the aryl nucleus by one to three halogen atom or alkyl radicals of 1 to 3 carbon atoms;
10. a hydroxyalkyl radical of 2 to 5 carbon atoms;
11. a dialkylaminoalkyl radical of 4 to 8 carbon atoms;
12. a carbamoylalkyl radical of 2 to 8 carbon atoms;
13. an alkylcarbamoylalkyl radical of 3 to 8 carbon atoms;
14. a dialkylcarbamoylalkyl radical of 4 to 8 carbon atoms; or
15. an alkanoylalkyl radical of 3 to 8 carbon atoms;
$R^2$, $R^3$, $R^4$ and $R^5$, which may be the same or different, stand for
16. hydrogen atoms or
17. halogen atoms; or for
18. alkyl radicals of 1 to 5 carbon atoms;
19. haloalkyl radicals of 1 to 5 carbon atoms;
20. alkoxy radicals of 1 to 5 carbon atoms;
21. alkylthio radicals of 1 to 5 carbon atoms;
22. hydroxy radicals;
23. thiol radicals;
24. alkanoylamino radicals of 1 to 5 carbon atoms;
25. alkanoyloxy radicals of 1 to 5 carbon atoms;
26. aroyloxy radicals of 7 to 10 carbon atoms, optionally substituted in the aryl nucleus by one to three halogen atoms or alkyl radicals of 1 to 3 carbon atoms;
27. arylalkenoyloxy radicals of 9 to 12 carbon atoms;
28. hydroxyalkyl radicals of 1 to 5 carbon atoms;
29. alkylsulphinyl radicals of 1 to 5 carbon atoms; or
30. alkanesulphonyloxy radicals of 1 to 5 carbon atoms;
and the pharmaceutically-acceptable acid-addition salts thereof.

It is to be understood that when $R^1$ is an alkenyl, haloalkenyl or alkynyl radical, the double or triple bond it contains is separated from the nitrogen atom of the spiropiperidine ring by at least one carbon atom, and when $R^1$ is a hydroxyalkyl or dialkylaminoalkyl radical, the oxygen or nitrogen atom it contains is separated from the nitrogen atom of the spiropiperidine ring by at least two carbon atoms.

The numbering system used in this specification to describe the position of a substituent on the xanthene nucleus is as follows:

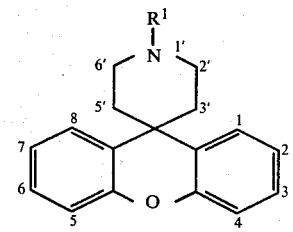

Reference to substitution at a particular position means substitution at that numbered position in the xanthene nucleus as defined immediately above.

A particular value for $R^1$ when it is an alkyl radical is such a radical of 1 to 8 carbon atoms, for example a methyl, ethyl, n-propyl, i-propyl, n-butyl, i-butyl, s-butyl, t-butyl, n-pentyl or n-hexyl radical.

A particular value for $R^1$ when it is an alkenyl radical is such a radical of 3 to 7 carbon atoms, for example allyl, 2-methylprop-2-enyl or 3-methylbut-2-enyl radical.

A particular value for $R^1$ when it is a haloalkenyl radical is such a radical of 3 or 4 carbon atoms, for example a 3-chloroprop-2-enyl radical.

A particular value for $R^1$ when it is an alkynyl radical is such a radical of 3 or 4 carbon atoms, for example a propargyl radical.

A particular value for $R^1$ when it is a cycloalkylalkyl radical is a cyclopropylmethyl or cyclobutylmethyl radical.

A particular value for $R^1$ when it is an arylalkyl radical is a benzyl or phenethyl radical.

A particular value for $R^1$ when it is an aroylalkyl radical is a 3-(4-fluorobenzoyl)propyl radical.

A particular value for $R^1$ when it is a hydroxyalkyl radical is a 2-hydroxyethyl, 2-hydroxypropyl or 2-hydroxy-1-methylethyl radical.

A particular value for $R^1$ when it is a dialkylaminoalkyl radical is such a radical of 4 to 6 carbon atoms, for example a 2-dimethylaminoethyl radical.

A particular value for $R^1$ when it is a carbamoylalkyl radical is such a radical of 2 to 4 carbon atoms, for example a carbamoylmethyl radical.

A particular value for $R^1$ when it is an alkylcarbamoylalkyl radical is such a radical of 3 to 5 carbon atoms, for example a methylcarbamoylmethyl radical.

A particular value for $R^1$ when it is a dialkylcarbamoylalkyl radical is such a radical of 4 to 6 carbon atoms, for example a dimethylcarbamoylmethyl radical.

A particular value for $R^1$ when it is an alkanoylalkyl radical is such a radical of 3 to 6 carbon atoms, for example an acetylmethyl radical.

A particular value for $R^2$, $R^3$, $R^4$ or $R^5$ when it is a halogen atom is a fluorine, chlorine or bromine atom.

A particular value for $R^2$, $R^3$, $R^4$ or $R^5$ when it is an alkyl radical is such a radical of 1 to 3 carbon atoms, for example a methyl radical.

A particular value for $R^2$, $R^3$, $R^4$ or $R^5$ when it is a haloalkyl radical is such a radical of 1 to 3 carbon atoms, for example a trifluoromethyl radical.

A particular value for $R^2$, $R^3$, $R^4$ or $R^5$ when it is an alkoxy radical is such a radical of 1 to 3 carbon atoms, for example a methoxy radical.

A particular value for $R^2$, $R^3$, $R^4$ or $R^5$ when it is an alkylthio radical is such a radical of 1 to 3 carbon atoms, for example a methylthio radical.

A particular value for $R^2$, $R^3$, $R^4$ or $R^5$ when it is an alkanoylamino radical is such a radical of 1 to 3 carbon atoms, for example an acetylamino radical.

A particular value for $R^2$, $R^3$, $R^4$ or $R^5$ when it is an alkanoyloxy radical is such a radical of 1 to 3 carbon atoms, for example an acetoxy radical.

A particular value for $R^2$, $R^3$, $R^4$ or $R^5$ when it is an aroyloxy radical is a 4-chlorobenzoyloxy radical.

A particular value for $R^2$, $R^3$, $R^4$ or $R^5$ when it is an arylalkenoyloxy radical is such a radical of 9 or 10 carbon atoms, for example a cinnamoyloxy radical.

A particular value for $R^2$, $R^3$, $R^4$ or $R^5$ when it is a hydroxyalkyl radical is such a radical of 1 to 3 carbon atoms, for example a hydroxymethyl radical.

A particular value for $R^2$, $R^3$, $R^4$ or $R^5$ when it is an alkylsulphinyl radical is such a radical of 1 to 3 carbon atoms, for example a methylsulphinyl radical.

A particular value for $R^2$, $R^3$, $R^4$ or $R^5$ when it is an alkanesulphonyloxy radical is such a radical of 1 to 3 carbon atoms, for example a methanesulphonyloxy radical.

Particular groups of compounds of the invention, each substituent being described by number as defined above, are as follows:

Those wherein $R^1$ is as defined above and $R^2$, $R^3$, $R^4$ and $R^5$ stand for values 16, 17, 18, 19, 20, 21, 22, 23, 24, 25, 26 or 28, for example hydrogen, fluorine, chlorine or bromine atoms or methyl, trifluoromethyl, methoxy, methylthio, hydroxy, thiol, acetylamino, acetoxy, 4-chlorobenzoyloxy, hydroxymethyl or 1-hydroxyethyl radicals, provided that when $R^2$ and $R^3$ are both other than hydrogen they are the same and when $R^4$ and $R^5$ are both other than hydrogen they are the same.

Further particular groups of compounds of the invention are as follows:

$R^1 = 1$ or 2
$R^2 = 20, 21, 22, 23, 25$ or 26 substituted at the 4-position
$R^3, R^4, R^5 =$ hydrogen $R^1 = 1$ or 2
$R^2 =$ hydroxy, methoxy or acetoxy substituted at the 4-position
$R^3, R^4, R^5 =$ hydrogen $R^1 =$ hydrogen, methyl or ethyl
$R^2 = 20, 21, 22, 23, 25$ or 26 substituted at the 4-position
$R^3, R^4, R^5 =$ hydrogen $R^1 =$ hydrogen, methyl or ethyl
$R^2 =$ hydroxy, methoxy or acetoxy substituted at the 4-position
$R^3, R^4, R^5 =$ hydrogen $R^1 = 1, 2, 3, 4, 5, 6, 7, 8, 9, 10, 11, 12, 13, 14$ or 15
$R^2 = 17, 18, 19, 20, 21$ or 28 substituted at the 2- or 3-position
$R^3, R^4, R^5 =$ hydrogen $R^1 = 2, 3, 6, 8, 9, 10, 11, 12, 13$ or 14
$R^2 =$ chlorine, bromine, methyl, trifluoromethyl, methoxy, methylthio or 1-hydroxyethyl substituted at the 2- or 3-position
$R^3, R^4, R^5 =$ hydrogen $R^1 = 2$ or 9
$R^2 =$ chlorine, bromine, methyl, trifluoromethyl, methoxy, methylthio or 1-hydroxyethyl substituted at the 2- or 3-position
$R^3, R^4, R^5 =$ hydrogen $R^1 =$ methyl or 3-(4-fluorobenzoyl)propyl
$R^2 =$ chlorine, bromine, methyl, trifluoromethyl, methoxy, methylthio or 1-hydroxyethyl substituted at the 2- or 3-position
$R^3, R^4, R^5 =$ hydrogen $R^1 = 1, 2, 3, 4, 5, 6, 7, 8, 9, 10, 11, 12, 13, 14$ or 15
$R^2 = 20, 21, 22, 23, 24, 25, 26$ or 27 substituted at the 4-position
$R^4 = 17, 18, 19, 20, 21, 22$ or 29 substituted at the 6-, 7- or 8-position
$R^3, R^5 =$ hydrogen $R^1 = 1, 2, 3, 4, 5, 6, 7, 8, 9, 10, 11, 12, 13, 14$ or 15
$R^2 = 20, 21, 22, 23, 24, 25, 26$ or 27 substituted at the 4-position
$R^4 = 17, 18, 19, 20, 21$ or 22 substituted at the 6-, 7- or 8-position
$R^3, R^5 =$ hydrogen $R^1 = 1, 2, 3, 4, 5, 6, 7, 8, 9, 10, 11, 12, 13, 14$ or 15
$R^2 =$ hydroxy, methoxy or acetoxy substituted at the 4-position
$R^4 = 17, 18, 19, 20, 21, 22$ or 29 substituted at the 6-, 7- or 8-position
$R^3, R^5 =$ hydrogen $R^1 = 1, 2, 3, 4, 5, 6, 7, 8, 9, 10, 11, 12, 13, 14$ or 15
$R^2 =$ hydroxy, methoxy or acetoxy substituted at the 4-position
$R^4 = 17, 18, 19, 20, 21$ or 22 substituted at the 6-, 7- or 8-position
$R^3, R^5 =$ hydrogen $R^1 = 1, 2, 3, 4, 5, 6, 7, 8, 9, 10, 11, 12, 13, 14$ or 15
$R^2 = 20, 21, 22, 23, 24, 25, 26$ or 27 substituted at the 4-position
$R^4 =$ fluorine, chlorine, methyl, trifluoromethyl, methoxy, methylthio, hydroxy or methylsulphinyl substituted at the 6-, 7- or 8-position
$R^3, R^5 =$ hydrogen $R^1 = 1, 2, 3, 4, 5, 6, 7, 8, 9, 10, 11, 12, 13, 14$ or 15
$R^2 = 20, 21, 22, 23, 24, 25, 26$ or 27 substituted at the 4-position
$R^4 =$ fluorine, chlorine, methyl, trifluoromethyl, methoxy, methylthio or hydroxy substituted at the 6-, 7- or 8-position
$R^3, R^5 =$ hydrogen $R^1 = 2, 3, 4, 5$ or 6
$R^2 = 20, 21, 22, 23, 24, 25, 26$ or 27 substituted at the 4-position $R^4$=17, 18, 19, 20, 21, 22 or 29 substituted at the 6-, 7- or 8-position
$R^3$, $R^5$=hydrogen
$R^1$=2, 3, 4, 5 or 6
$R^2$=20, 21, 22, 23, 24, 25, 26 or 27 substituted at the 4-position
$R^4$=17, 18, 19, 20, 21 or 22 substituted at the 6-, 7- or 8-position
$R^3$, $R^5$=hydrogen
$R^1$=2, 3, 4, 5 or 6
$R^2$=hydroxy, methoxy or acetoxy substituted at the 4-position
$R^4$=17, 18, 19, 20, 21, 22 or 29 substituted at the 6-, 7- or 8-position
$R^3$, $R^5$=hydrogen
$R^1$=2, 3, 4, 5 or 6
$R^2$=hydroxy, methoxy or acetoxy substituted at the 4-position
$R^4$=17, 18, 19, 20, 21 or 22 substituted at the 6-, 7- or 8-position
$R^3$, $R^5$=hydrogen
$R^1$=2, 3, 4, 5 or 6
$R^2$=20, 21, 22, 23, 24, 25, 26 or 27 substituted at the 4-position
$R^4$=fluorine, chlorine, methyl, trifluoromethyl, methoxy, methylthio, hydroxy or methylsulphinyl substituted at the 6-, 7- or 8-position
$R^3$, $R^5$=hydrogen
$R^1$=2, 3, 4, 5 or 6
$R^2$=20, 21, 22, 23, 24, 25, 26 or 27 substituted at the 4-position
$R^4$=fluorine, chlorine, methyl, trifluoromethyl, methoxy, methylthio or hydroxy substituted at the 6-, 7- or 8-position
$R^3$, $R^5$=hydrogen
$R^1$=methyl
$R^2$=20, 21, 22, 23, 24, 25, 26 or 27 substituted at the 4-position
$R^4$=17, 18, 19, 20, 21, 22 or 29 substituted at the 6-, 7- or 8-position
$R^3$, $R^5$=hydrogen
$R^1$=methyl
$R^2$=20, 21, 22, 23, 24, 25, 26 or 27 substituted at the 4-position
$R^4$=17, 18, 19, 20, 21 or 22 substituted at the 6-, 7- or 8-position
$R^3$, $R^5$=hydrogen
$R^1$=methyl
$R^2$=hydroxy, methoxy or acetoxy substituted at the 4-position
$R^4$=17, 18, 19, 20, 21, 22 or 29 substituted at the 6-, 7- or 8-position
$R^3$, $R^5$=hydrogen
$R^1$=methyl
$R^2$=hydroxy, methoxy or acetoxy substituted at the 4-position
$R^4$=17, 18, 19, 20, 21 or 22 substituted at the 6-, 7- or 8-position
$R^3$, $R^5$=hydrogen
$R^1$=methyl
$R^2$=20, 21, 22, 23, 24, 25, 26 or 27 substituted in the 4-position
$R^4$=fluorine, chlorine, methyl, trifluoromethyl, methoxy, methylthio, hydroxy or methylsulphinyl substituted at the 6-, 7- or 8-position
$R^3$, $R^5$=hydrogen
$R^1$=methyl $R^2$=20, 21, 22, 23, 24, 25, 26 or 27 substituted at the 4-position
$R^4$=fluorine, chlorine, methyl, trifluoromethyl, methoxy, methylthio or hydroxy substituted at the 6-, 7- or 8-position
$R^3$, $R^5$=hydrogen
$R^1$=methyl
$R^2$=methoxy, hydroxy or acetoxy substituted at the 4-position
$R^4$=fluorine, chlorine, methoxy, methylthio, hydroxy or methylsulphinyl substituted at the 6-position or fluorine or chlorine substituted at the 7- or 8-position
$R^3$, $R^5$=hydrogen
$R^1$=methyl
$R^2$=methoxy, hydroxy or acetoxy substituted at the 4-position
$R^4$=fluorine, chlorine, methoxy, methylthio or hydroxy substituted at the 6-position or fluorine or chlorine substituted at the 7- or 8-position
$R^3$, $R^5$=hydrogen
$R^1$=methyl
$R^2$=hydroxy, methoxy or acetoxy substituted at the 4-position
$R^3$=hydrogen
$R^4$, $R^5$=fluorine or chlorine (same or different)

Particular compounds of the invention are described in the Examples and of those the preferred compound is that wherein
$R^1$=methyl
$R^2$=hydroxy substituted at the 4-position
$R^4$=chlorine substituted at the 6-position
$R^3$, $R^5$=hydrogen
and the salts thereof as defined above.

A suitable pharmaceutically-acceptable acid-addition salt of the invention is, for example, a hydrochloride, hydrobromide, phosphate or sulphate, or a citrate, acetate, maleate or oxalate.

The xanthene derivative of the invention may be manufactured by methods known in themselves for the manufacture of chemically analogous compounds, $R^1$, $R^2$, $R^3$, $R^4$ and $R^5$ having the meanings stated above, for example:

(a) for those compounds in which $R^1$ has a value other than those numbered 1, 4, 5, 10, 12, 13 or 15 and $R^2$, $R^3$, $R^4$ and $R^5$ have values other than those numbered 19, 22, 23, 24, 25, 26, 27, 28 or 30, reacting a compound of the formula III:

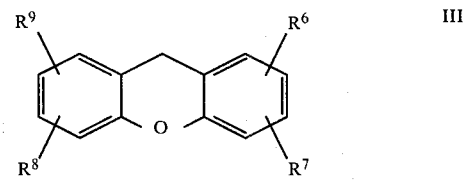

wherein $R^6$, $R^7$, $R^8$ and $R^9$ have the values stated above for $R^2$, $R^3$, $R^4$ and $R^5$ respectively other than those numbered 19, 22, 23, 24, 25, 26, 27, 28 or 30 with a compound of the formula $R^{10}N(CH_2CH_2X)_2$ wherein $R^{10}$ has the value stated above for $R^1$ other than that numbered 1, 4, 5, 10, 12, 13 or 15 and wherein X is a displaceable radical. X may be, of example, a displaceable halogen atom, for example a chlorine or bromine atom, or an arenesulphonyloxy or alkanesulphonyloxy radical, for example a toluene-p-sulphonyloxy or methanesulphonyloxy radical. The reaction is preferably conducted in the presence of a base, for example sodium methylsulphinylmethide, in a diluent or solvent, for example dimethyl sulphoxide, and is preferably conducted in an inert atmosphere.

(b) for those compounds in which $R^1$ has a value other than that numbered 12, 13, 14 or 15 and $R^2$, $R^3$, $R^4$ and $R^5$ have values other than those numbered 19, 24, 25, 26, 27 or 30, reducing a compound of the formula IV:

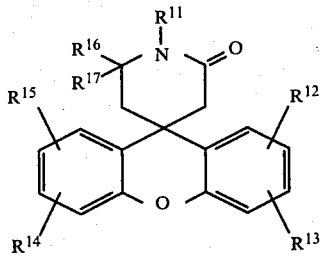

wherein $R^{11}$ has the value stated above for $R^1$ other than that numbered 12, 13, 14 or 15, $R^{12}$, $R^{13}$, $R^{14}$ and $R^{15}$ have the values stated above for $R^2$, $R^3$, $R^4$ and $R^5$ other than those numbered 19, 24, 25, 26, 27 or 30 and wherein $R^{16}$ and $R^{17}$ stand for hydrogen atoms or together stand for an oxygen atom. The reduction may be carried out with a complex metal hydride, for example lithium aluminum hydride, in a diluent or solvent, for example diethyl ether or tetrahydrofuran, and may be accelerated or completed by the application of heat, for example by heating to the boiling point of the diluent or solvent.

(c) for those compounds in which $R^1$ has a value other than that numbered 3, 4, 5, 10, 11, 12, 13 or 14 and $R^2$, $R^3$, $R^4$ and $R^5$ have values other than those numbered 20, 23, 24, 25, 26, 27, 28 or 30, cyclisation of a compound of the formula V:

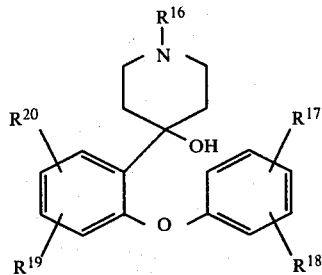

wherein $R^{16}$ has the value stated above for $R^1$ other than that numbered 3, 4, 5, 10, 11, 12, 13 or 14 and $R^{17}$, $R^{18}$, $R^{19}$ and $R^{20}$ have the values stated above for $R^2$, $R^3$, $R^4$ and $R^5$ other than those numbered 20, 23, 24, 25, 26, 27, 28 or 30. The cyclisation may be carried out with a strong acid, for example sulphuric or polyphosphoric acid, and the reaction may be accelerated or completed by the application of heat, for example by heating to about 100° C.

(d) for those compounds in which $R^1$ has a value other than that numbered 11, 12, 13, 14 or 15 and $R^2$, $R^3$, $R^4$ and $R^5$ have values other than those numbered 19, 25, 26 or 27, reaction of a compound of the formula VI:

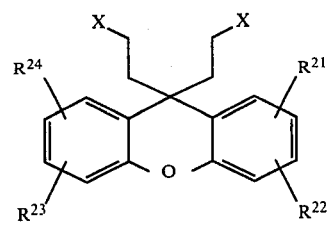

wherein $R^{21}$, $R^{22}$, $R^{23}$ and $R^{24}$ have the values stated above for $R^2$, $R^3$, $R^4$ and $R^5$ other than those numbered 19, 25, 26 or 27 with a compound of the formula $R^{25}NH_2$ wherein $R^{25}$ has the value stated above for $R^1$ other than that numbered 11, 12, 13, 14 or 15. The reaction may be conducted by heating the reactants in a diluent or solvent, for example ethanol or xylene. Where a temperature higher than the boiling point of the diluent or solvent is required, the reaction may be conducted in a pressure vessel. Alternatively where the boiling point of the reactant of the formula $R^{25}NH_2$ is sufficiently high, no diluent or solvent may be required.

(e) for those compounds in which $R^1$ is an alkyl or cycloalkylalkyl radical, $R^2$ is a hydrogen atom or an alkyl radical and one of $R^3$, $R^4$ and $R^5$ is a hydroxy, alkoxy, hydroxymethyl or thiol radical and the remaining two members of $R^3$, $R^4$ and $R^5$ are hydrogen atoms, quenching an anion of the formula VII:

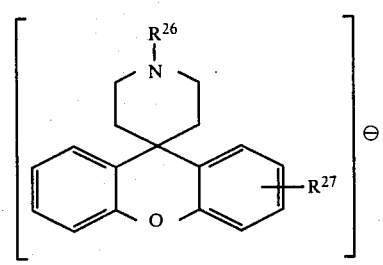

wherein $R^{26}$ is an alkyl or cycloalkylalkyl radical and $R^{27}$ is a hydrogen atom or an alkyl or alkoxy radical. The reaction may be conducted in a diluent or solvent, for example hexane, in an inert atmosphere. The anion is quenched with a reagent which gives rise to a hydroxy, alkoxy, hydroxymethyl or thiol radical, for example hydrogen peroxide, t-butyl perbenzoate, paraformaldehyde or sulphur respectively.

(f) for those compounds in which $R^1$ is an alkyl, cycloalkylalkyl or arylalkyl radical and $R^2$, $R^3$, $R^4$ and $R^5$ have values other than those numbered 19, 24, 25, 26, 27 or 30, reducing a compound of the formula VIII:

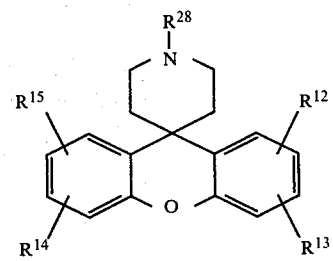

wherein $R^{12}$, $R^{13}$, $R^{14}$ and $R^{15}$ have the meanings stated above and wherein $R^{28}$ is an alkanoyl, cycloalkylalkanoyl or arylalkanoyl radical. The reduction may be carried out with a complex metal hydride, for example lithium aluminium hydride, in a diluent or solvent, for example diethyl ether or tetrahydrofuran, and it may be accelerated or completed by the application of heat, for example by heating to the boiling point of the diluent or solvent.

(g) for those compounds in which $R^1$ is a hydrogen atom and $R^2$, $R^3$, $R^4$ and $R^5$ have values other than those numbered 21, 23, 24, 25, 26, 27 or 30, replacement by hydrogen of the alkyl or arylalkyl radical in a compound of the formula IX:

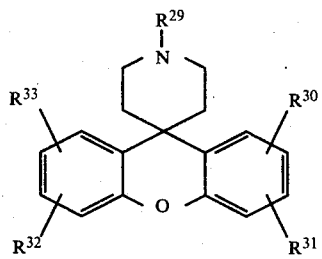

IX wherein $R^{29}$ is an alkyl or arylalkyl radical and $R^{30}$, $R^{31}$, $R^{32}$ and $R^{33}$ have the values stated above for $R^2$, $R^3$, $R^4$ and $R^5$ other than those numbered 21, 23, 24, 25, 26, 27 or 30. When $R^{29}$ is an α-arylalkyl radical, for example the benzyl radical, it may be replaced by hydrogen by hydrogenolysis, for example by hydrogenation in the presence of a palladium-on-charcoal catalyst in a diluent or solvent. The hydrogen may be at atmospheric pressure or it may be at a pressure of up to 10 atmospheres. When $R^{29}$ is an alkyl or arylalkyl radical, for example a methyl, isopropyl or benzyl radical, it may be replaced by hydrogen by treatment with an alkyl or aryl chloroformate, for example ethyl or phenyl chloroformate, followed by hydrolysis of the alkyl- or aryloxycarbonyl derivative thus obtained. The hydrolysis may be carried out by heating with a base, for example sodium or potassium hydroxide, in a diluent or solvent, for example ethanol or aqueous ethanol.

(h) for those compounds in which $R^1$ is other than a hydrogen atom and $R^2$, $R^3$, $R^4$ and $R^5$ have values other than those numbered 21, 22, 23, or 24, reaction of a compound of the formula X:

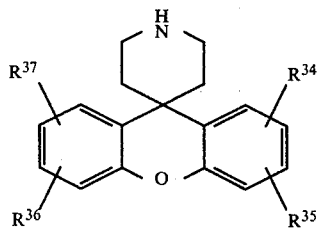

X wherein $R^{34}$, $R^{35}$, $R^{36}$ and $R^{37}$ have the values stated above for $R^2$, $R^3$, $R^4$ and $R^5$ other than those numbered 21, 22, 23 or 24, with a compound of the formula $R^{38}$-Y wherein $R^{38}$ has the values stated above for $R^1$ other than a hydrogen atom and Y is a displaceable halogen atom. Y may be, for example, a chlorine or bromine atom and the reaction may be conducted in the presence of a base, for example sodium bicarbonate or sodium hydride, in a diluent or solvent, for example dimethyl formamide. The reaction may be accelerated or completed by the application of heat, for example by heating to the boiling point of the diluent or solvent.

(i) for those compounds in which $R^1$ is a haloalkenyl radical and $R^2$, $R^3$, $R^4$ and $R^5$ have values other than those numbered 20, 21, 25, 26, 27 or 30, addition of a hydrogen halide to the triple bond in a compound of the formula XI:

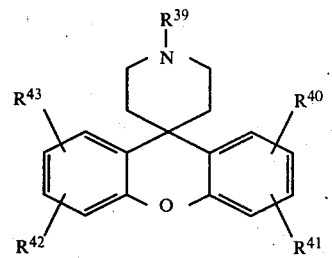

XI wherein $R^{39}$ is an alkynyl radical and $R^{40}$, $R^{41}$, $R^{42}$ and $R^{43}$ have the values stated above for $R^2$, $R^3$, $R^4$ and $R^5$ other than those numbered 20, 21, 25, 26, 27 or 30. The hydrogen halide may be, for example, hydrogen chloride and it may be added to the triple bond by reaction with pyridine hydrochloride, (j) for those compounds in which $R^1$ has a value other than that numbered 3, 4 or 5 and in which at least one of $R^2$, $R^3$, $R^4$ and $R^5$ is a hydroxy radical and the remaining members of $R^2$, $R^3$, $R^4$ and $R^5$ have values other than that numbered 27, replacement by hydrogen of the benzyl group in a compound of the formula XII:

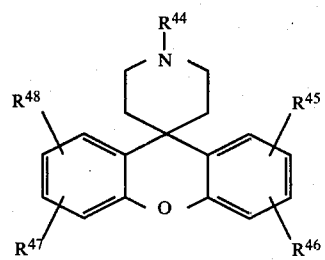

XII wherein $R^{44}$ has the value stated above for $R^1$ other than that numbered 3, 4 or 5 and at least one of $R^{45}$, $R^{46}$, $R^{47}$ and $R^{48}$ is a benzyloxy radical and the remaining members of $R^{45}$, $R^{46}$, $R^{47}$ and $R^{48}$ have the values stated above for $R^2$, $R^3$, $R^4$ and $R^5$ other than that numbered 27. The benzyl group may be replaced by hydrogen by reaction with hydrogen in the presence of a palladium-on-charcoal catalyst or by reaction with an acid, for example aqueous ethanolic hydrochloric acid.

(k) for those compounds in which $R^1$ has a value other than that numbered 5 and in which at least one of $R^2$, $R^3$, $R^4$ and $R^5$ is a hydroxy radical and the remaining members of $R^2$, $R^3$, $R^4$ and $R^5$ have values other than those numbered 20, 21, 25, 27 or 30, replacement by hydrogen of the alkyl part of the alkoxy radical in a compound of the formula XIII:

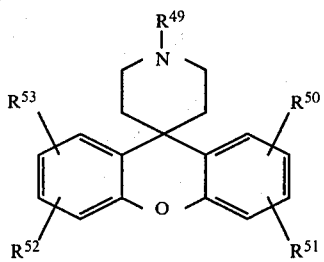

XIII

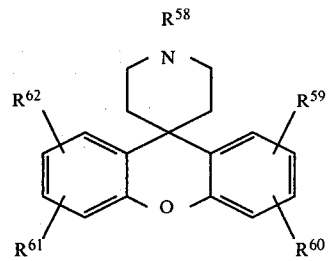

XV wherein $R^{49}$ has the value stated above for $R^1$ other than that numbered 5 and in which at least one of $R^{50}$, $R^{51}$, $R^{52}$ and $R^{53}$ is an alkoxy radical and the remaining members of $R^{50}$, $R^{51}$, $R^{52}$ and $R^{53}$ have the values stated above for $R^2$, $R^3$, $R^4$ and $R^5$ other than those numbered 20, 21, 25, 27 or 30. The reaction may be carried out with an acid, for example with HBr in acetic acid at reflux or with aqueous 48% w/v HBr at reflux; with boron tribromide in a solvent such as methylene chloride; with pyridine hydrochloride, for example by heating at 200° C.; with sodium ethanethiolate or sodium thiophenoxide, for example by heating in a solvent such as dimethyl formamide at 100°–150° C. under argon; or with lithium iodide.

(1) for those compounds in which at least one of $R^2$, $R^3$, $R^4$ and $R^5$ is a hydroxy radical and the remaining members of $R^2$, $R^3$, $R^4$ and $R^5$ have values other than those numbered 25, 26, or 27, hydrolysis of the acyloxy radical in a compound of the formula XIV:

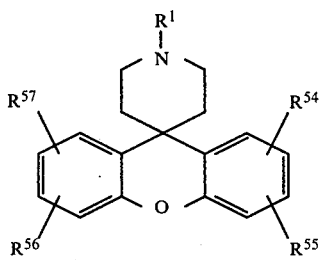

XIV wherein at least one of $R^{54}$, $R^{55}$, $R^{56}$ and $R^{57}$ is an acyloxy radical and the remaining members of $R^{54}$, $R^{55}$, $R^{56}$ and $R^{57}$ have the values stated above for $R^2$, $R^3$, $R^4$ and $R^5$ other than those numbered 25, 26 or 27. The acyloxy radical may be such a radical of up to 10 carbon atoms, for example an acetoxy or benzoyloxy radical. The hydrolysis may be carried out with a dilute acid or base, for example 3NHCl.

(m) for those compounds in which $R^1$ has a value other than that numbered 3, 4, 5, 7, 8, 9 or 15 and at least one of $R^2$, $R^3$, $R^4$ and $R^5$ is a halogen atom and the remaining members of $R^2$, $R^3$, $R^4$ and $R^5$ have values other than those numbered 21, 23 or 27, halogenation of a compound of the formuula XV:

wherein $R^{58}$ has the value stated above for $R^1$ other than that numbered 3, 4, 5, 7, 8, 9 or 15 and $R^{59}$, $R^{60}$, $R^{61}$ and $R^{62}$ have the values stated above for $R^2$, $R^3$, $R^4$ and $R^5$ other than those numbered 21, 23 or 27, at least one being hydrogen. The halogenation may be carried out using a molecular halogen, for example bromine, in a diluent or solvent such as chloroform, or by using an N-halo derivative such as N-chlorosuccinimide.

(n) for those compounds in which $R^1$ has a value other than that numbered 1 or 10, at least one of $R^2$, $R^3$, $R^4$ and $R^5$ has a value numbered 25, 26, 27 or 30 and the remaining members of $R^2$, $R^3$, $R^4$ and $R^5$ have values other than those numbered 22, 23 or 28, reaction of a compound of the formula XVI:

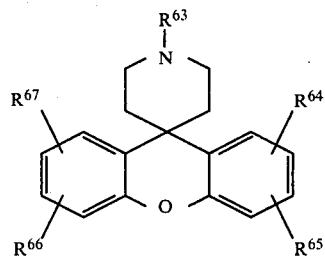

XVI wherein $R^{63}$ has the value stated above for $R^1$ other than that numbered 1 or 10, at least one of $R^{64}$, $R^{65}$, $R^{66}$ and $R^{67}$ is a hydroxy radical and the remaining members of $R^{64}$, $R^{65}$, $R^{66}$ and $R^{67}$ have the values stated above for $R^2$, $R^3$, $R^4$ and $R^5$ other than those numbered 22, 23 or 28, with an alkanoic, arylalkanoic, arylalkenoic or alkanesulphonic acid, or with an acylating agent derived therefrom. The acid may be, for example, acetic acid, p-chlorobenzoic acid, cinnamic acid or methanesulphonic acid and the acylating agent derived therefrom may be, for example, the corresponding acid chloride or anhydride. The reaction is preferably carried out in a basic solvent such as pyridine.

(o) for those compounds in which $R^1$ has a value other than that numbered 1 or 10, at least one of $R^2$, $R^3$, $R^4$ and $R^5$ is an alkanoylamino radical and the remaining members of $R^2$, $R^3$, $R^4$ and $R^5$ have values other than those numbered 22, 23 or 28, reaction of a compound of the formula XVII:

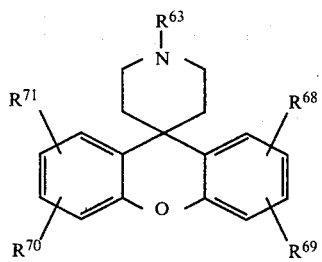

XVII wherein $R^{63}$ has the value stated above, at least one of $R^{68}$, $R^{69}$, $R^{70}$ and $R^{71}$ is an amino radical and the remaining members of $R^{68}$, $R^{69}$, $R^{70}$ and $R^{71}$ have the values stated above for $R^2$, $R^3$, $R^4$ and $R^5$ other than those numbered 22, 23 or 28, with an alkanoic acid or an acylating agent derived therefrom. The reactant may be, for example, acetic acid or the corresponding acid chloride or anhydride. The reaction is preferably carried out in a diluent or solvent, for example ether.

(p) for those compounds in which $R^1$ is an alkyl radical, heating a compound of the formula XVIII:

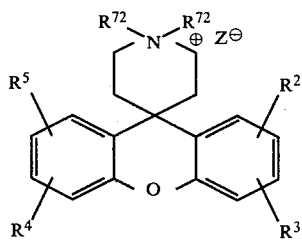

XVIII wherein $R^{72}$ is an alkyl radical and Z is a chlorine, bromine or iodine atom. When $R^7$ is a methyl radical, the reaction is conveniently carried out by heating to 200° C. in vacuo.

(q) for those compounds in which at least one of $R^2$, $R^3$, $R^4$ and $R^5$ is an alkylsulphinyl radical and the remaining members of $R^2$, $R^3$, $R^4$ and $R^5$ have values other than that numbered 21 or 23, oxidation of a compound of the formula XIX:

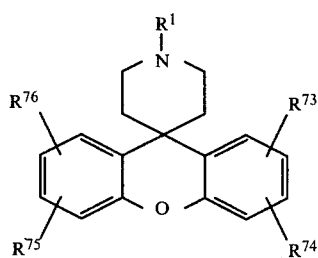

XIX wherein at least one of $R^{73}$, $R^{74}$, $R^{75}$ and $R^{76}$ is an alkylthio radical and the remaining members of $R^{73}$, $R^{74}$, $R^{75}$ and $R^{76}$ have the values stated above for $R^2$, $R^3$, $R^4$ and $R^5$ other than that numbered 23. The reaction may be carried out with a mild oxidising agent such as sodium periodate, hydrogen peroxide or iodobenzene dichloride.

(r) for those compounds wherein $R^1$ is an aroylalkyl or alkanoylalkyl radical and $R^2$, $R^3$, $R^4$ and $R^5$ have values other than those numbered 25, 26 or 27, hydrolysis of a compound of the formula XX:

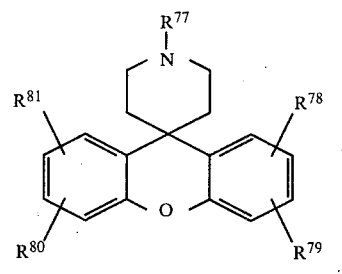

XX wherein $R^{77}$ is a ketal derived from an aroylalkyl or alkanoylalkyl radical and $R^{78}$, $R^{79}$, $R^{80}$ and $R^{81}$ have the values stated above for $R^2$, $R^3$, $R^4$ and $R^5$ other than those numbered 25, 26 or 27. The ketal may, for example, be a dimethyl or ethylene ketal. The hydrolysis is preferably carried out with a dilute mineral acid, for example by warming with 3 N aqueous HCl.

The xanthene derivative of the invention may be converted into a pharmaceutically-acceptable acid-addition salt by conventional means.

The starting materials for use in the processes of the invention may be prepared, from known compounds, as described in the Examples. The following summary illustrates the general reactions involved.

The starting material of the formula III for use in process (a) may be prepared by reaction of the appropriate 2-chlorobenzoic acid with the appropriate phenol as described in Example 32. The resulting acid is cyclised to the corresponding xanthene as described in Example 33, and the xanthone is reduced to the corresponding xanthene as described in Example 34. The preparation of 2-fluoro-5-methoxyxanthone is described in Example 35.

The starting material of the formula IV for use in process (b) may be prepared by dialkylation of the appropriate xanthene with 2-chloroethyl vinyl ether. The product is oxidised with chromic acid to give the spiro-4'-tetrahydropyran-2'-one which is reacted with the appropriate amine to give the corresponding N-substituted spiro-4'-piperidin-2'-one. Alternatively the appropriate xanthene may be dialkylated with allyl bromide, the resulting 9,9-diallyl derivative oxidised with potassium permanganate/sodium metaperiodate and the resulting diacid cyclised to the corresponding 6-membered anhydride with acetic anhydride. Reaction with the appropriate amine then gives the corresponding monoacid-monoamide which is thereafter cyclised with acetic anhydride to give the N-substituted spiro-4'-piperidin-2',6'-dione.

The starting material of the formula V for use in process (c) may be prepared by reaction of the anion derived from the appropriate diphenyl ether with the appropriate N-substituted 4-piperidone. The anion may be formed by reaction with butyl lithium.

The starting material of the formula VI for use in process (d) may be prepared by hydrolysis of the divinyl ether of the appropriate 9,9-bis(2-hydroxyethyl)xanthene followed by reaction of the resulting diol with a reagent which replaces OH with a displaceable radical, for example a halogenating agent or methanesulphonyl chloride.

The anion of the formula VII used as starting material in process (e) may be prepared by abstraction of a proton from the corresponding neutral xanthene derivative, for example with butyl lithium.

The starting material of the formula VIII for use in process (f) may be prepared by reacting the free NH compound with the appropriate carboxylic acid or acylating agent derived therefrom.

The starting material of the formula XVII for use in process (o) may be prepared by employing process (e) and quenching the anion with hydroxylamine methyl ether. Alternatively the appropriate amino derivative can be prepared using the route described in Example 35 and 34 to prepare the appropriate nitroxanthene. The spiropiperidine ring can then be formed using process (a) or (d) and the nitro group subsequently reduced to an amino group.

The starting material of the formula XVIII for use in process (p) may be prepared by treatment of the dimethanesulphonate ester of the appropriate 9,9-bis(2-hydroxyethyl)-xanthene with the appropriate dialkylamine followed by treatment of the resulting quaternary methanesulphonate in an ion-exchange column.

The starting material of the formula XIX for use in process (q) may be obtained by repeating process (h) using the appropriate alkylating agent.

The preparations of specific starting materials are described inter alia in Examples 2, 3, 7, 10, 14, 17, 19, 21, 22, 24, 27 and 29, and also in Examples 32–35.

The compounds of the invention have analgesic activity in warm-blooded animals. This is demonstrated by activity in a number of standard tests for detecting analgesic activity, for example the mouse writhing test (Collier et al., *Brit. J. Pharmac. Chemother.*, 1963, 32, 295; Whittle, *Brit. J. Pharmac. Chemother.*, 1964, 22, 246) and the mouse tail clip test (Bianchi and Franceschini, *Brit. J. Pharmac. Chemother*, 1954, 9, 280). These tests are carried out as follows:

*Tail clip test*

10 Female mice of bodyweight approximately 20 g. each are dosed subcutaneously with the compound under test. Twenty minutes later the mice are placed in a plastic arena (30 cm. diameter) and an artery clip is placed in the tail at a distance of 1 cm. from the rump. If an individual mouse does not respond to the painful stimulus of the clip within a 10 second period, it is recorded as analgesed. In this way 50% analgesia corresponds to 5 mice in 10 showing a negative response to the clip.

*Writhing test*

A painful stimulus is produced by injection of a 0.25% v/v aqueous solution of acetic acid or a 0.03% w/w aqueous solution of acetylcholine into the peritoneum of a female mouse. The characteristic response to this pain is an abdominal constriction in conjunction with a stretching of the body.

Acetic Acid method

Of 12 20 g. female mice, 6 are dosed either subcutaneously or orally with the compound under test and the remaining 6 act as controls. Twenty minutes later all 12 mice receive an injection of the acetic acid solution (0.4 ml.) and are then placed into a plastic container divided into twelve compartments. The number of writhes of each mouse are then recorded over a 15 minute period starting 3 minutes after injection of the agent. The total number of writhes recorded for the treated group are then totalled and compared with the total found for the control group. The results are expressed as % analgesia as follows:

$$100 - \left( \frac{\text{Drug group}}{\text{Control group}} \times 100 \right)$$

Acetylcholine method

Of 12 20 g. female mice, 6 are dosed either subcutaneously or orally with the compound under test and the remaining 6 act as controls. Thirty minutes later all the 12 mice receive an intraperitoneal injection of 0.2 ml. of the acetylcholine solution, and are placed on a plastic platform (30 cm. diameter). Mice which do not writhe during the minute immediately after the injection are said to be analgesed.

The results are expressed as % analgesia as follows:

$$\frac{\text{No. of dosed animals not writhing}}{\text{No. of controls writhing}} \times 100$$

(On average approximately 95% of controls respond to the acetylcholine challenge)

All the compounds exemplified in this specification are active on at least one of these standard tests at a dose of equal to or less than 100 mg./kg. of the free base. The compound of the invention 6-chloro-4-hydroxy-1'-methylxanthene-9-spiro-4'-piperidine has an oral $LD_{50}$ in mice of greater than 200 mg./kg. The $LD_{50}$ of the same compound when dosed intravenously is greater than 25 mg./kg. Other $LD_{50}$ values for compounds of the invention when dosed intravenously are as follows:

| $R^1$ | $R^2$ | $R^3$ | $R^4$ | $LD_{50}$ (mg./kg.) |
|---|---|---|---|---|
| 4-OAc | H | 6-Cl | H | >35 |
| 4-OAc | H | 6-SMe | H | >40 |
| 4-OH | H | 8-F | H | >20 |
| 4-OAc | H | 6-OMe | H | >20 |

Within the analgesics of the present invention, at least four sub-classes can be identified:
1. Compounds in which $R^2$, $R^3$, $R^4$ and $R^5$ are other than values 20, 21, 22, 23, 24, 25, 26 or 27 substituted at the 4- or 5-position are neuroleptic analgesics, that is analgesics of the methotrimeprazine type, having a strong sedative component.
2. Compounds in which $R^1$ is a hydrogen atom or a methyl or ethyl radical, $R^2$ has value 20, 21, 22, 23, 24, 25, 26 or 27 substituted at the 4-position and $R^3$, $R^4$ and $R^5$ are hydrogen atoms are narcotic analgesics, that is analgesics of the morphine type with a range of activities from codeine to morphine.
3. Compounds in which $R^1$ is other than hydrogen, a methyl or ethyl radical, $R^2$ has value 20, 21, 22, 23, 24, 25, 26 or 27 substituted at the 4-position and $R^3$, $R^4$ and $R^5$ are hydrogen atoms are partial agonist analgesics, that is analgesics, of the pentazocine type, which partially antagonise the effect of morphine.
4. Compounds in which $R^1$ is hydrogen or methyl, $R^2$ has value 20, 21, 22, 23, 24, 25, 26 or 27 substituted at the 4-position, $R^4$ has value 17, 18, 19, 20, 21, 22 or 29 substituted at the 6-, 7- or 8-position and $R^3$ and $R^5$ are hydrogen atoms have varying mixtures of analgesic and sedative properties.

According to a further feature of the invention there is provided a pharmaceutical composition which comprises as active ingredient a xanthene derivative of the invention in association with a non-toxic pharmaceutically-acceptable diluent or carrier.

The pharmaceutical composition may be, for example, in a form suitable for oral, parenteral or rectal administration, for which purposes it may be formulated by means known to the art into the form of, for example, tablets, capsules, aqueous or oily solutions or suspensions, emulsions, sterile injectable aqueous or oily solutions or suspensions, dispersible powders or suppositories.

The pharmaceutical composition of the invention may also contain, in addition to the xanthene derivative, one or more known drugs selected from other analgesic agents, for example aspirin, paracetamol, phenacetin, codeine, pethidine, and morphine, anti-inflammatory agents, for example naproxen, indomethacin and ibuprofen, neuroleptic agents such as chlorpromazine, prochlorperazine, trifluoperazine and haloperidol and other sedative drugs and tranquillisers such as chlordiazepoxide, phenobarbitone and amylobarbitone.

A preferred pharmaceutical composition of the invention is one suitable for oral administration in unit dosage form, for example tablets and capsules, which contain between 1 and 200 mg. of active ingredient, or one suitable for intravenous, intramuscular or subcutaneous injection, for example a sterile aqueous solution containing between 1 and 50 mg./ml. of active ingredient.

The pharmaceutical composition of the invention will normally be administered to man for the treatment or prevention of pain at such a dose that each patient receives an oral dose of between 30 mg. and 300 mg. of active ingredient, an intramuscular or subcutaneous dose of between 30 and 150 mg. of active ingredient or an intravenous dose of between 15 and 75 mg. of active ingredient, the composition being administered 2 or 3 times per day.

The invention is illustrated, but not limited, by the following Examples in which Examples 32 to 35 illustrate the preparation of starting materials:

EXAMPLE 1

A solution of xanthene (9.1 g.) in dimethyl sulphoxide (75 ml.) is added dropwise over 20 minutes at room temperature to a solution of sodium methylsulphinylmethide [prepared in the usual way from sodium hydride (8 g. of a 60% dispersion in mineral oil) and dimethyl sulphoxide (100 ml.)] with stirring in an atmosphere of nitrogen. The blood-red mixture is stirred at room temperature for a further 30 minutes, cooled to 0° C., and a solution of N-methyldi-(2-chloroethyl)amine (9.6 g.) in dimethyl sulphoxide (20 ml.) is then added dropwise during 15 minutes, keeping the temperature below 20° C. Water (500 ml.) is added to the new colourless mixture, and the mixture is extracted three times with ether. The combined ether extracts are dried over $MgSO_4$, evaporated to dryness and the gummy residue (12.2 g.) is chromatographed on basic alumina (Brockmann Grade III), eluting with increasing concentrations of chloroform in light petroleum (b.p. 60°–80° C.). Elution with 5% chloroform in light petroleum gives, on evaporation of the solvent, a gum which is dissolved in ether and treated with ethereal hydrochloric acid. The solid is recrystallised from ethanol-ether to give 1'-methylxanthene-9-spiro-4'-piperidine hydrochloride, m.p. 220°–222° C.

EXAMPLE 2

A mixture of 1'-methylxanthene-9-spiro-4'-piperidin-2'-one (50 mg.), lithium aluminium hydride (25 mg.) and dry tetrahydrofuran (15 ml.) is heated under reflux for 3 hours. Dilute sodium hydroxide solution is added, and the mixture is filtered through diatomaceous earth. The tetrahydrofuran is removed from the filtrate by evaporation under reduced pressure, and the aqueous residue is extracted with ether. The ethereal extract is dried over $MgSO_4$ and treated with ethereal hydrochloric acid. The solid is recrystallised from ethanol-ether to give 1'-methylxanthene-9-spiro-4'-piperidine hydrochloride, m.p. 220°–222° C.

The 1'-methylxanthene-9-spiro-4'-piperidine-2'-one used as starting material may be obtained as follows:

A solution of xanthene (18.2 g.) in dimethyl sulphoxide (150 ml.) is added dropwise over 20 minutes at room temperature to a solution of sodium methylsulphinylmethide [prepared in the usual way from sodium hydride (12 g. of a 60% dispersion in mineral oil) and dimethyl sulphoxide (150 ml.)] with stirring in an atmosphere of nitrogen. The blood-red mixture is stirred at room temperature for a further 30 minutes, cooled to 10° C., and 2-chloroethyl vinyl ether (21.3 g.) is then added dropwise during 30 minutes. Water (750 ml.) is added to the now colourless mixture, and the mixture is extracted three times with ether. The combined ether extracts are dried over $MgSO_4$ and evaporated to dryness. The residue of 9,9-bis(2'-vinyloxyethyl)xanthene (28.0 g.) is dissolved in acetone (150 ml.) and treated with excess Jones reagent (chromic acid in acetone) at 10° C. Methanol is then added, and the solvent is evaporated. To the residue water is added, and the mixture is extracted three times with ethyl acetate. The combined extracts are washed with saturated sodium hydrogen carbonate solution, then with water, dried over $MgSO_4$ and evaporated to dryness. The solid residue is recrystallised from ethanol to give xanthene-9-spiro-4'-tetrahydropyran-2'-one, m.p. 156°–159° C.

A mixture of xanthene-9-spiro-4'-tetrahydropyran-2'-one (0.5 g.) and methylamine (5 ml.) is heated at 250° C. for 4 hours in a steel bomb. The gummy residue (0.52 g.) is chromatographed on silica gel, eluting with increasing concentrations of chloroform in light petroleum (b.p. 60°–80° C.). Elution with 25% chloroform in light petroleum gives, on evaporation of the solvent, a solid residue which is recrystallised from ethanol to give 1'-methylxanthene-9-spiro-4'-piperidin-2'-one, m.p. 158°–159° C.

EXAMPLE 3

A mixture of 9,9-di(2'-methanesulphonyloxyethyl)-xanthene (0.21 g.) and phenethylamine (0.36 g.) is heated on the steam-bath under nitrogen for 20 hours. Ether is added, an insoluble solid is filtered off and the filtrate is treated with ethereal hydrochloric acid. The precipitate is filtered off, washed with water, and crystallised from ethanol-ether to give 1'-phenethylxanthene-9-spiro-4'-piperidine hydrochloride, m.p. 275° C. (with decomposition).

The 9,9-di(2'-methanesulphonyloxyethyl)xanthene used as starting material may be prepared as follows:

A mixture of 9,9-bis(2'-vinyloxyethyl)xanthene (57 g.) (prepared as in Example 2), water (400 ml.) and concentrated hydrochloric acid (15 ml.) is heated on the steambath with vigorous stirring for 5 hours. The cooled mixture is extracted three times with ether and the combined extracts are dried over MgSO₄ and evaporated to dryness. The solid residue is recrystallised from chloroform-light petroleum (b.p. 60°-80° C.) to give 9,9-bis(2'-hydroxyethyl)xanthene, m.p. 144°-145° C. Methanesulphonyl chloride (588 mg.) is added dropwise over 5 minutes at 5° C. to a solution of 9,9-bis(2'-hydroxyethyl)xanthene (0.54 g.) in dry pyridine (5 ml.) with stirring. The mixture is allowed to stand at room temperature for 20 hours and is then poured into a mixture of 3 N hydrochloric acid (20 ml.) and ice (10 g.), and the resulting mixture is extracted with ethyl acetate. The ethyl acetate extract is washed with 3 N hydrochloric acid and water, dried over MgSO₄, and evaporated to dryness. The solid residue is recrystallised from acetone-light petroleum (b.p. 60°-80° C.) to give 9,9-bis(2'-methanesulphonyloxyethyl)-xanthene, m.p. 121°-122° C.

EXAMPLE 4

1'-Methyl-4-methoxyxanthene-9-spiro-4'-piperidine hydrochloride (1.0 g.) in a solution of 45% w/v hydrobromic acid in glacial acetic acid (10 ml.) is heated under reflux for 2 hours. The solution is basified with sodium bicarbonate, diluted with water and extracted with chloroform. The chloroform extract is washed with water, dried over MgSO₄, and evaporated to dryness. The residue is recrystallised from toluene-petroleum ether (b.p. 60°-80° C.) to give 1'-methyl-4-hydroxyxanthene-9-spiro-4'-piperidine, m.p. 171°-173° C.

The 1'-methyl-4-methoxyxanthene-9-spiro-4'-piperidine hydrochloride used as starting material may be obtained by the method described in Example 1 using an equivalent amount of 4-methoxyxanthene instead of xanthene. The product is recrystallised from ethanol-ether and has m.p. 234°-236° C.

EXAMPLE 5

1'-Methyl-4-hydroxyxyanthene-9-spiro-4'-piperidine hydrochloride (0.3 g.) in dry pyridine (10 ml.) is treated with excess acetic anhydride for 12 hours at room temperature. Pyridine and acetic anhydride are removed in vacuo and the residue dissolved in chloroform and treated with ethereal hydrochloric acid. The solvent is removed and the residue recrystallised from iso-propanol-light petroleum to give 1'-methyl-4-acetoxyxanthene-9-spiro-4'-piperidine hydrochloride, m.p. 216°-220° C.

EXAMPLE 6

The process described in Example 1 is repeated using the equivalent amount of the appropriate substituted xanthene as starting material instead of xanthene. The following compounds are thus prepared:

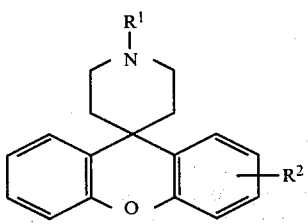

| $R^1$ | $R^2$ | Salt | m.p.(°C.) |
|---|---|---|---|
| Me | 2-Cl | HCl | 238 |
| Me | 4-Cl | HCl | 196–197 |
| Me | 2-Me | HCl | 230 |
| Me | 2-CF₃ | HCl | 305–306 |
| Me | 3-OMe | Maleate | 141–143 |

EXAMPLE 7

A mixture of 4-methoxy-9,9-di(2'-methanesulphonyloxyethyl)xanthene (4.7 g.) and a 33% (w/v) solution of ethylamine in ethanol (15 ml.) is heated in a carius tube at 150° C. for 3 hours. Water is added to the cooled mixture and the ethanol is evaporated off. The mixture is extracted with ether and the ether extract is washed with saturated potassium carbonate solution and water, dried with MgSO₄ and treated with ethereal hydrochloric acid. The gummy residue is crystallised from ethanol-ether to give 1'-ethyl-4-methoxyxanthene-9-spiro-4'-piperidine hydrochloride, m.p. 222°-224° C.

The above process is repeated using equivalent amounts of the appropriate xanthene and amine as starting materials. The following compounds are thus obtained:

| $R^1$ | $R^2$ | Salt | m.p.(° C.) | Solvent |
|---|---|---|---|---|
| —CH₂CH₃ | H | HCl | 247–248 | ethanol-ether |
| —CH₂CH₂CH₃ | H | HCl | 269–272 | ethanol-ether |
| —CH(CH₃)—CH₃ | H | HCl | 244–246 | ethanol-ether |
| —CH₂CH₂CH₂CH₃ | H | HCl | 268–270 | ethanol-ether |
| —CH₂CH=CH₂ | H | HCl | 232–235 | ethanol-ether |
| —(CH₂)₄CH₃ | H | HCl | 265–270 | ethanol-ether |
| —(CH₂)₅CH₃ | H | HCl | 260–264 | ethanol-ether |
| *—CH₂—C₆H₅ | H | HCl | 242–245 | ethanol-ether |
| *—CH₂CH₂—C₆H₅ | H | HCl | 265–270 | ethanol-ether |
| —CH₂—CH(CH₂)(CH₂) (cyclopropyl) | H | HCl | 258–261 | ethanol-ether |
| —CH₂CH₂CH₃ | OCH₃ | HCl | 254–256 | ethanol-ether |
| —CH₂CH=CH₂ | OCH₃ | HCl | 212–214 | ethanol-ether |
| —CH₂—CH(CH₂)(CH₂) (cyclopropyl) | OCH₃ | HCl | 228–230 | ethanol-ether |
| —CH₂CH(CH₃)—CH₃ | OCH₃ | HCl | 215–217 | ethyl acetate-methanol |
| —CH₂CH₂OH | OCH₃ | oxalate | 190–192 | ethyl acetate-methanol |
| —C(CH₃)₂CH₃ | OCH₃ | oxalate | 235 (decomp.) | ethyl acetate-methanol |
| —CH₂C≡CH | OCH₃ | oxalate | 226–228 | ethyl acetate- |

-continued

[Structure: xanthene-9-spiro-4'-piperidine with R¹ on N and R² on aromatic ring]

| R¹ | R² | Salt | m.p.(° C.) | Solvent |
|---|---|---|---|---|
| —CH₂C(CH₃)=CH₂ | OCH₃ | oxalate | 222–226 | methanol ethyl acetate-methanol |
| —CH(CH₃)—CH₂CH₃ | OCH₃ | oxalate | 212 (decomp.) | ethyl acetate-methanol |
| —CH(CH₃)(CH₃) [—CH(CH₃)₂ type, isopropyl branch] —CH< with CH₃, CH₃ | OCH₃ | oxalate | 228 (decomp.) | methanol-ether |
| —CH(CH₃)—CH₂OH | OCH₃ | oxalate | 205 (decomp.) | methanol-ether |
| —CH₂CH(OH)—CH₃ | OCH₃ | oxalate | 200 (decomp.) | methanol-ether |
| *—CH₂—C₆H₅ | OCH₃ | HCl | 241–242 | ethyl acetate-methanol |
| *—CH₂CH₂—C₆H₅ | OCH₃ | Free base | 142–144 | — |
| *—C₆H₅ | OCH₃ | oxalate | 192 (decomp.) | methanol-ether |

*These compounds are prepared by heating a mixture of the reactants under reflux in xylene for 0.5–3 hours.

The 4-methoxy-9,9-di(2'-methanesulphonyloxyethyl)xanthene used as starting material may be prepared by repeating the second part of Example 2, and the second and third parts of Example 3 using 4-methoxyxanthene as starting material and there is thus obtained 4-methoxy-9,9-bis(2'-vinyloxyethyl)xanthene, m.p. 138° C., 4-methoxy-9,9-bis(2'-hydroxyethyl)xanthene, m.p. 140°–142° C. and 4-methoxy-9,9-bis(2'-methanesulphonyloxyethyl)xanthene, m.p. 152°–154° C. respectively.

EXAMPLE 8

A solution of 1'-benzyl-4-methoxyxanthene-9-spiro-4'-piperidine hydrochloride (3.0 g.) in absolute ethanol (100 ml.) is hydrogenated using 5% palladium on carbon catalyst, at 4 atmospheres pressure and 50° C. The catalyst is filtered off and the solvent evaporated to dryness. The residue is crystallised from ethanol-ether to give 4-methoxyxanthene-9-spiro-4'-piperidine, m.p. 214°–216° C.

EXAMPLE 9

A mixture of 4-methoxyxanthene-9-spiro-4'-piperidine (2.0 g.), 1-bromo-3-methylbut-2-ene (1.15 g.), sodium bicarbonate (0.59 g.) and dimethylformamide (20 ml.) is heated under reflux for 4 hours. The mixture is cooled, poured into water and extracted with chloroform. The chloroform extract is washed with water, dried with MgSO₄ and evaporated to give a gummy residue. The residue is dissolved in isopropanol and treated with ethereal hydrochloric acid. The residue is recrystallised from isopropanol-ether to give 1'-(3-methylbut-2-enyl)-4-methoxyxanthene-9-spiro-4'-piperidine hydrochloride, m.p. 247°–249° C.

EXAMPLE 10

A mixture of 1'-cyclopropylcarbonyl-4-methoxyxanthene-9-spiro-4'-piperidine (5.3 g.), lithium aluminum hydride (4.5 g.) and dry tetrahydrofuran (200 ml.) is heated under reflux for 4 hours. Water (4.5 ml.), 3 N sodium hydroxide solution (4.5 ml.) and water (13.5 ml.) are added and the mixture filtered. The tetrahydrofuran is removed by evaporation. The gummy residue is dissolved in ether and treated with ethereal hydrochloric acid. The solid is recrystallised from ethanol-ether to give 1'-cyclopropylmethyl-4-methoxyxanthene-9-spiro-4'-piperidine hydrochloride, m.p. 228°–230° C. The 1'-cyclopropylcarbonyl-4-methoxyxanthene-9-spiro-4'-piperidine used as starting material may be prepared as follows:

A solution of cyclopropane carboxylic acid chloride (1.2 ml.) in methylene chloride (10 ml.) is added dropwise with stirring to a mixture of 4-methoxyxanthene-9-spiro-4'-piperidine (2.0 g.) and triethylamine (1.6 ml.) in methylene chloride (40 ml.) at 5° C. The mixture is allowed to reach room temperature and stirred overnight. The mixture is washed with 3 N hydrochloric acid, 3 N sodium hydroxide solution and water, dried MgSO₄ and the methylene chloride evaporated to dryness, to give 1'-cyclopropylcarbonyl-4-methoxyxanthene-9-spiro-4'-piperidine (I.R. amide band 1620 cm.⁻¹; t.l.c.—single spot) which is used without further purification.

EXAMPLE 11

The demethylation process described in Example 4 is repeated, either using the method described in Example 4 or by one of the methods described below, and using the appropriate methoxyxanthene derivative as starting material in place of 1'-methyl-4-methoxyxanthene-9-spiro-4'-piperidine. The following compounds are thus prepared:

[Structure: xanthene-9-spiro-4'-piperidine with R¹ on N, and R², R³ on aromatic ring]

| R¹ | R² | R³ | Method | Salt | m.p.(°C.) | Solvent |
|---|---|---|---|---|---|---|
| H | H | OH | A | HCl | >300 | ethanol-ether |

-continued

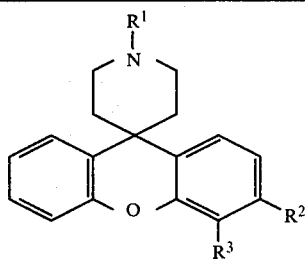

| R¹ | R² | R³ | | Salt | m.p.(°C) | Solvent |
|---|---|---|---|---|---|---|
| —CH₂CH₃ | H | OH | C | Free base | 164–166 | ether-P.E. (b.p.60–80° C.) |
| —CH₂CH₂CH₃ | H | OH | B | HCl | * | |
| —CH₂CH=CH₂ | H | OH | B | HCl | 150 (decomp.) | ethanol-ether |
| —CH₂CH(CH₂CH₂) (cyclopropyl) | H | OH | B | HCl | 226–227 | ethanol-ether |
| —CH₂—CH—CH₂ \| \| CH₂—CH₂ ** | H | OH | B | HCl | * | |
| —CH₂—CH=C(CH₃)₂ | H | OH | B | HCl | * | |
| —CH₂CH(CH₃)CH₃ | H | OH | D | oxalate | 200 (decomp.) | methanol ethyl acetate |
| —C(CH₃)₃ | H | OH | D | HCl acetate | 203–205 173–176 | methanol-ether ethyl acetate-P.E.(b.p. 80–100° C.) |
| —CH₂—C(CH₃)=CH₂ | H | OH | F | oxalate | 200 (decomp.) | methanol-ether |
| —CH(CH₃)CH₂CH₃ | H | OH | D | oxalate | 165 (decomp.) | methanol ethyl acetate |
| —CH(CH₃)—CH₃ | H | OH | D | HCl | 152 (decomp.) | methanol-ether |
| —CH(CH₃)CH₂OH | H | OH | F | oxalate | 195 (decomp.) | methanol-ether |
| —CH₂CH₂—C₆H₅ | H | OH | D | oxalate | 250 | methanol ethyl acetate |
| —C₆H₅ | H | OH | D | HCl | 222–224 | methanol-ether |
| —CH₃ | —OH | H | D | Free base | 220–239 | ethyl acetate-petrol ether (b.p.60–80° C.) |

*Structure determined by mass spectrometry as follows:

| R¹ | M⊕ | m/e |
|---|---|---|
| —CH₂CH₂CH₃ | 309 | 99 |
| —CH₂—CH—CH₂ \| \| CH₂—CH₂ | 335 | 125 |
| —CH₂—CH=C(CH₃)₂ | 335 | 125 |

EXAMPLE 12

The process described in Example 5 is repeated using an equivalent amount of the appropriate hydroxyxanthene as starting material in place of 1'-methyl-4-hydroxyxanthene-9-spiro-4'-piperidine. The following compounds are thus obtained.

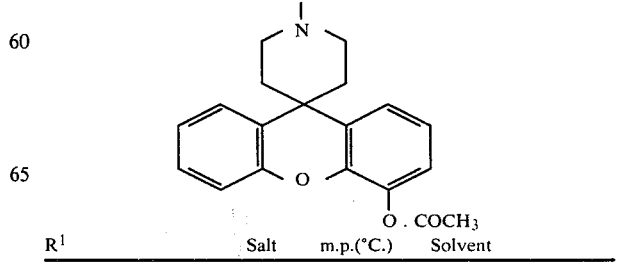

| R¹ | Salt | m.p.(°C.) | Solvent |
|---|---|---|---|

| | | | |
|---|---|---|---|
| —CH₂—CH(CH₂)(CH₂) (cyclopropyl-CH₂) | HCl | 214–218 | isopropanol-petroleum ether b.p. 60–80° C. |
| —CH₂—CH(CH₃)(CH₃) | HCl | 231–233 | ethyl acetate ether |

EXAMPLE 13

A mixture of 1'-methylxanthene-9-spiro-4'-piperidine hydrochloride (7.5 g.), bromine (6 ml.) and chloroform (250 ml.) is heated under reflux for 20 hours. The solution is washed with dilute sodium hydroxide solution and water, dried over MgSO₄, and evaporated to dryness. The solid residue is dissolved in ethanol and treated with ethereal hydrochloric acid. The solid is recrystallised from ethanol-ether to give 1'-methyl-2,7-dibromoxanthene-9-spiro-4'-piperidine hydrochloride, m.p. 292°–295° C. (decomp.)

EXAMPLE 14

To a solution of 1'-methylxanthene-9-spiro-4'-piperidine (1.3 g.) in hexane (25 ml.) in an argon atmosphere is added a 1.6 molar solution of t-butyl lithium in pentane (3.5 ml.) with stirring at room temperature. The mixture is stirred for 1 hour at room temperature. Hydroxylamine methyl ether (0.4 g.) in hexane (5 ml.) is added dropwise during 5 minutes. Water is added and the organic layer separated, washed with water and dried with MgSO₄. The solvent is evaporated to give a solid residue, which is recrystallised from hexane to give 1'-methyl-4-aminoxanthene-9-spiro-4'-piperidine, m.p. 173°–174° C. The above process is repeated using an equivalent amount of sulphur and paraformaldehyde as starting material in place of hydroxylamine methyl ether. The following compounds are thus prepared:

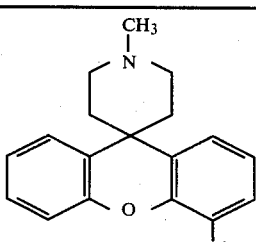

| R¹ | Salt | m.p.(°C.) | Solvent |
|---|---|---|---|
| —SH | oxalate | 190–192 | methanol-ether |
| —CH₂OH | Free base | 167–169 | ether-petroleum ether b.p. 60–80° C. |

EXAMPLE 15

A mixture of 1'-methyl-4-aminoxanthene-9-spiro-4'-piperidine (0.06 g.) and acetic anhydride (0.5 ml.) in ether (20 ml.) is stirred at room temperature for 0.5 hour. The ether solution is washed with saturated sodium carbonate solution and water, dried with MgSO₄ and the ether evaporated to give a gummy residue. The residue is crystallised from hexane to give 1'-methyl-4-acetamidoxanthene-9-spiro-4'-piperidine, m.p. 176°–178° C.

EXAMPLE 16

A mixture of 1'-(prop-2-ynyl)-4-methoxyxanthene-9-spiro-4'-piperidine hydrogen oxalate (1.3 g.) and pyridine hydrochloride prepared from pyridine (9 ml.) and concentrated hydrochloric acid (10 ml.) is heated at 200° C. for 10 minutes. The mixture is cooled and water (20 ml.) added. The solution is basified with dilute sodium carbonate solution and extracted with ether. The ether extract is washed with water, dried with MgSO₄ and evaporated to dryness. The solid residue is recrystallised from ethyl acetate petroleum ether (b.p. 80°–100° C.) to give 1'-(3-chloro-prop-2-enyl)-4-hydroxyxanthene-9-spiro-4'-piperidine, m.p. 153°–155° C.

EXAMPLE 17

The process described in Example 2 is repeated using 1'-methylxanthene-9-spiro-4'-piperidin-2',6'-dione in place of 1'-methylxanthene-9-spiro-4'-piperidin-2'-one as starting material and there is thus obtained 1'-methylxanthene-9-spiro-4'-piperidine hydrochloride, m.p. 220°–222° C.

The 1'-methylxanthene-9-spiro-4'-piperidin-2',6'-dione used as starting material may be prepared as follows:

Xanthene (9 g.) is dialkylated as in Example 1 except that allyl bromide is used as alkylating agent instead of N-methyldi-(2-chlorethyl)amine. The crude product is chromatographed on silica gel and 9,9-diallylxanthene is eluted with petroleum ether (b.p. 60°–80° C.). The product is obtained as a gum and its structure verified by nuclear magnetic resonance.

Without further purification, 9,9-diallylxanthene in t-butanol (75 ml.) is added dropwise to a stirred solution of potassium permanganate (0.2 g.), sodium metaperiodate (35 g.) and potassium carbonate (10 g.) in water (250 ml.) and left overnight. The solution is acidified with dilute hydrochloric acid and extracted with ethyl acetate. Xanthene 9,9-diacetic acid is extracted from the organic layer with sodium hydrogen carbonate solution and after recovery by acidification recrystallised from ethyl acetate-petroleum ether (b.p. 60°–80° C.), m.p. 187°–188° C.

A solution of xanthene 9,9-diacetic acid (0.8 g.) in acetic anhydride (3 ml.) is heated under reflux for 1 hour, cooled and poured into water. Extraction with ethyl acetate gives xanthene-9-spiro-4'-tetrahydropyran-2',6'-dione which is recrystallised from ethyl acetate-petroleum ether (b.p. 60°–80° C.), m.p. 188°–190° C.

This anhydride is treated with excess aqueous methylamine at room temperature. After ten minutes, the solution is acidified with dilute hydrochloric acid and the monoacid-monoamide is filtered and dried. Without further purification it is treated with excess acetic anhydride at reflux for 0.5 hours, and the reaction mixture then poured into cold aqueous sodium bicarbonate. The product, extracted with ethyl acetate, is chromatographed on silica gel and eluted with 2% ethyl acetate-petroleum ether (b.p. 60°–80° C.), giving 1'-methylxanthene-9-spiro-4'-piperidin-2',6'-dione which is recrystallised from ethyl acetate-petroleum ether (b.p. 60°–80° C.), m.p. 148°–149° C.

EXAMPLE 18

A mixture of 4-acetoxyxanthene-9-spiro-4'-piperidine hydrochloride (0.69 g.), propargyl bromide (0.24 g.), potassium carbonate (0.4 g.) or sodium hydride (0.12 g. of an 80% w/w dispersion in oil) and dimethylformamide (10 ml.) is stirred at room temperature for 3 hours. The mixture is poured into water and extracted with ethyl acetate. The ethyl acetate extract is washed with water, dried with MgSO4 and evaporated to give a gummy residue. The residue is dissolved in ether and the precipitate obtained on treatment with ethereal hydrochloric acid recrystallised from ethanol-ether to give 4-acetoxy-1'-(prop-2-ynyl)xanthene-9-spiro-4'-piperidine hydrochloride, m.p. 118°–120° C.

The above process is repeated using equivalent amounts of the appropriate alkylating halide, and the following are thus obtained:

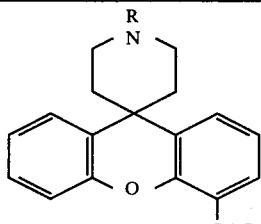

| R | Salt | m.p.(°C.) | Halide |
|---|---|---|---|
| —CH2COCH3 | HCl ¼ H2O | 252–254 | ClCH2COCH3 |
| —CH2CONHMe | HCl | 233–236 | BrCH2CONHMe |
| —CH2CH=CH2 | HCl | 225–227 | BrCH2CH=CH2 |
| —CH2CONMe2 | HCl ¾ H2O | 210–213 | BrCH2CONMe2 |

The 4-acetoxyxanthene-9-spiro-4'-piperidine hydrochloride used as starting material may be prepared in the following way:

1'-Benzyl-4-methoxyxanthene-9-spiro-4'-piperidine is demethylated using 45% w/v hydrobromic acid in glacial acetic acid as described in Example 4 to give 1'-benzyl-4-hydroxyxanthene-9-spiro-4'-piperidine converted to its hydrochloride, m.p. 164° C. on recrystallisation from ethanol-ether.

The 1'-benzyl-4-hydroxyxanthene-9-spiro-4'-piperidine is acetylated using acetic anhydride in pyridine as described in Example 5 to give 4-acetoxy-1'-benzylxanthene-9-spiro-4'-piperidine hydrochloride, m.p. 234°–236° C. on recrystallisation from ethanol-ether.

A solution of 4-acetoxy-1'-benzylxanthene-9-spiro-4'-piperidine hydrochloride (13.5 g.) in ethanal (200 ml.) is hydrogenated using 5% w/w palladium-on-carbon catalyst, at 1 atmosphere and 25° C. The catalyst is filtered off and the solvent evaporated to dryness. The residue is crystallised from ethanol-ether to give 4-acetoxyxanthene-9-spiro-4'-piperidine hydrochloride, m.p. 162°–165° C.

EXAMPLE 19

The quaternary chloride 1',1'-dimethyl-4-methoxyxanthene-9-spiro-4'-piperidinium chloride is heated at 200°–220° C. under vacuum (0.1 mm.) for 1 hour. The cooled residue is dissolved in methanol, poured into water and extracted with ether. The dried ether solution is treated with anhydrous ethereal hydrochloric acid to give 4-methoxy-1'-methylxanthene-9-spiro-4'-piperidine hydrochloride, m.p. 232°–235° C.

The quaternary chloride used as starting material may be prepared as follows:

9,9-Bis-(2'-methanesulphonyloxyethyl)-4-methoxyxanthene (0.5 g.) is treated with excess ethanolic dimethylamine at reflux for 2 hours. The solution is evaporated to dryness and the residue triturated with toluene. The solid quaternary salt, 1',1'-dimethyl-4-methoxyxanthene-9-spiro-4'-piperidinium methanesulphonate dihydrate is recrystallised from methanol-ether, m.p. 215°–220° C.

The quaternary methanesulphonate (0.1 g.) is dissolved in methanol and passed down a strongly basic (quaternary amine) ion exchange column in the chloride form. The eluant is evaporated to dryness to give 1',1'-dimethyl-4-methoxyxanthene-9-spiro-4'-piperidinium chloride which is used without further purification.

EXAMPLE 20

4-Acetoxy-1'-(prop-2-ynyl)xanthene-9-spiro-4'-piperidine hydrochloride (0.4 g.) is stirred with 3 N hydrochloric acid (20 ml.) at room temperature for 24 hours. The solution is basified using solid sodium bicarbonate and extracted with ethyl acetate. The ethyl acetate extract is dried over MgSO4 and evaporated to give a gummy residue which is dissolved in ether and treated with ethereal hydrochloric acid. The precipitate is recrystallised from ethanol-ether to give 4-hydroxy-1'-(prop-2-ynyl)xanthene-9-spiro-4'-piperidine hydrochloride, m.p. 246°–247° C.

The above process is repeated using the appropriate 4-acetoxyxanthene derivative as starting material and the following compounds are thus obtained:

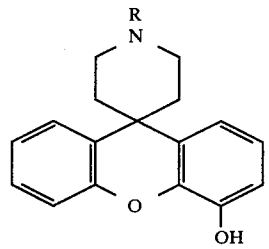

| R | Salt | m.p.(°C.) | Recrystallisation solvent |
|---|---|---|---|
| —CH2CONHMe | HCl H2O | 168 | Ethyl acetate |
| —CH2CONMe2 | HCl H2O | 184–186 | ethyl acetate |

EXAMPLE 21

A mixture of 4-hydroxy-1-methyl-4-(2'-phenoxy)-phenylpiperidine (0.5 g.) and polyphosphoric acid (5 g.) is heated on a steam-bath for 1 hour. The mixture is poured into 10 N ammonium hydroxide solution and extracted with chloroform. The chloroform extract is dried with MgSO4 and evaporated to give a gummy residue which is dissolved in ether and treated with ethereal hydrochloric acid. The precipitate obtained is recrystallised from ethanol-ether to give 1'-methylxanthene-9-spiro-4'-piperidine hydrochloride, m.p. 221°–223° C.

The 4-hydroxy-1-methyl-4-(2'-phenoxy)phenylpiperidine used as starting material may be prepared as follows:

A solution of n-butyl lithium in hexane (2.25 M., 45 ml.) is slowly added to a solution of diphenyl ether (8.5 g.) in sodium dried diethyl ether (200 ml.) under an atmosphere of argon. The mixture is stirred for 24 hours at room temperature, cooled to 0° C. and a solution of 1-methyl-4-piperidone (5.7 g.) in diethyl ether (25 ml.) is slowly added. The mixture is stirred at room temperature for 24 hours. Water is then carefully added and the organic layer is separated, dried with MgSO4 and evaporated to give a white solid which is recrystallised from ether to give 4-hydroxy-1-methyl-4-(2'-phenoxy)-phenylpiperidine, m.p. 118°–119° C.

EXAMPLE 22

A mixture of 4-methoxy-1'-methyl-6-(methylthio)xanthene-9-spiro-4'-piperidine (0.5 g.) and aqueous sodium metaperiodate (5 ml. of 0.5 M solution) is stirred until a solution is obtained. The reaction mixture is added to aqueous sodium bicarbonate and extracted with ethyl acetate. The ethyl acetate is evaporated and the organic basic residue is converted to its hydrochloride to give 4-methoxy-1'-methyl-6-methylsulphinylxanthene-9-spiro-4'-piperidine hydrochloride, m.p. 183°–185° C. on recrystallisation from ethanol-ether.

The 4-methoxy-1'-methyl-6-(methylthio)xanthene-9-spiro-4'-piperidine used as starting material may be prepared as follows:

A suspension of 3-chloro-5-methoxyxanthone (5 g.) in dimethylformamide is added to a solution of excess sodium thiomethoxide in dimethylformamide (prepared from methyl mercaptan and sodium hydride). After 1 hour the reaction mixture is poured into water and extracted with ether, giving on evaporation 5-methoxy-3-(methylthio)xanthone, m.p. 201°–203° C. on recrystallisation from methanol.

The process described in Example 34 is repeated using 5-methoxy-3-(methylthio)xanthone as starting material to give 5-methoxy-3-(methylthio)xanthene which is recrystallised from methanol and characterised by its infra-red spectrum. The process described in Example 25 is then repeated using 5-methoxy-3-(methylthio)xanthene as starting material and there is thus obtained 4-methoxy-1'-methyl-6-(methylthio)xanthene-9-spiro-4'-piperidine hydrochloride, m.p. 112°–114° C. on recrystallisation from ethanol-ether.

EXAMPLE 23

The process described in Example 22 is repeated using an equivalent amount of 4-hydroxy-1'-methyl-6-(methylthio)xanthene-9-spiro-4'-piperidine as starting material and there is thus obtained 4-hydroxy-1'-methyl-6-methylsulphinylxanthene-9-spiro-4'-piperidine hydrochloride hemihydrate, m.p. 282°–283° C.

EXAMPLE 24

A solution of 4-benzyloxy-6-methoxy-1'-methylxanthene-9-spiro-4'-piperidine hydrochloride (1.5 g.) in ethanol (200 ml.) is hydrogenated using 5% w/w palladiun-on-carbon catalyst at 1 atmosphere and 25° C. The catalyst is filtered off and the ethanol evaporated to give a gummy residue which is crystallised from ethanol-ether to give 4-hydroxy-6-methoxy-1'-methylxanthene-9-spiro-4'-piperidine hydrochloride, m.p. 223°–224° C.

The 4-benzyloxy-6-methoxy-1'-methylxanthene-9-spiro-4'-piperidine used as starting material may be prepared as follows:

To a solution of 3-chloro-5-methoxyxanthone (12.5 g.) [see Examples 32 and 33] in dry dichloromethane at 0° C. is slowly added boron tribromide (24 ml.). The mixture is stirred at room temperature for 24 hours, then poured into water. The resulting precipitate is filtered off and dried to give 3-chloro-5-hydroxyxanthone which is used without further purification.

The 3-chloro-5-hydroxyxanthone (11 g.) in dimethylformamide (50 ml.) is added to a suspension of sodium hydride (1.5 g.) in dimethylformamide (100 ml.). The mixture is stirred at room temperature for 15 minutes and benzyl bromide (6 ml.) is added dropwise. The mixture is poured into water/ice (600 ml.), extracted with chloroform and the chloroform extract dried with $MgSO_4$. Evaporation of the solvent gives a lightbrown solid which is recrystallised from ethanol to give 5-benzyloxy-3-chloroxanthone, m.p. 154° C.

A mixture of 5-benzyloxy-3-chloroxanthone (8.5 g.), sodium hydride (3 g.), methaol (20 ml.) and dimethylformamide (100 ml.) is stirred at room temperature for 24 hours. The mixture is poured into water and the precipitate is filtered. The residue is recrystallised from isopropanol to give 5-benzyloxy-3-methoxyxanthone, m.p. 158° C.

5-Benzyloxy-3-methoxyxanthone (3.5 g.) is reduced using a solution borane-tetrahydrofuran complex as described in Example 34 to give 5-benzyloxy-3-methoxyxanthene, m.p. 107°–108° C. on recrystallisation from methanol.

5-Benzyloxy-3-methoxyxanthene is reacted with N-methyldi-(2-chloroethyl)amine using the method described in Example 1 to give 4-benzyloxy-6-methoxy-1'-methylxanthene-9-spiro-4'-piperidine hydrochloride which is used without further purification.

EXAMPLE 25

The process described in Example 1 is repeated using the equivalent amount of the appropriate substituted xanthene as starting material instead of xanthene. The following compounds are thus obtained:

| $R^2$ | $R^3$ | Salt | m.p.(°C.) |
|---|---|---|---|
| 4-OMe | 6-OMe | HCl 1 $H_2O$ | 138–139 |
| 4-OMe | 6-Cl | HCl 2 $H_2O$ | 154–157 |
| 4-OMe | 7-$CF_3$ | HCl | 295–296 |
| 4-OMe | 6-SMe | HCl | 112–113 |
| 4-OMe | 2-Cl | HCl | 265–268 |
| 2,3-diCl | H | oxalate | 183–185 |
| 2-CH—Me<br>\|<br>OH | H | HCl ¼ $H_2O$ | 208–210 |
| 3-Cl | H | maleate | 174–176 |
| 4-OMe | 6-F | HCl 1 $H_2O$ | 114–117 |
| 4-OMe | 7-F | HCl ¼ $H_2O$ | 252–255 |
| 4-OMe | 8-F | HCl ¼ $H_2O$ | 195–200* |

*Recrystallised from isopropanol-ether.

EXAMPLE 26

A mixture of 1'-phenoxycarbonylxanthene-9-spiro-4'-piperidine (370 mg.), ethanol (80 ml.) and a 50% w/v solution of potassium hydroxide in water (20 ml.) is heated under reflux for 22 hours. The mixture is cooled and concentrated hydrochloric acid (20 ml.) is added and the ethanol is evaporated. The residue is washed with ether, water (50 ml.) is added and the resulting solution made alkaline with 3 N sodium hydroxide. The alkaline solution is extracted with chloroform and the chloroform extract is washed with water, dried ($MgSO_4$) and evaporated to dryness. The gummy residue is dissolved in ethanol and treated with ethereal hydrochloric acid. The solid is recrystallised from ethanol-ether to give xanthene-9-spiro-4'-piperidine hydrochloride, m.p. 248°-250° C.

The 1'-phenoxycarbonylxanthene-9-spiro-4'-piperidine used as starting material may be obtained as follows:

A solution of phenyl chloroformate (8 ml.) in methylene chloride (75 ml.) is added dropwise with stirring to a solution of 1'-methylxanthene-9-spiro-4'-piperidine (17.0 g.) in methylene chloride (200 ml.) at 5° C. The mixture is allowed to reach room temperature and stirred overnight. The mixture is washed successively with 3 N sodium hydroxide solution, 3 N hydrochloric acid and water, dried (MgSO₄) and the methylene chloride evaporated to dryness. The gummy residue is crystallised from methanol to give 1'-phenoxycarbonylxanthene-9-spiro-4'-piperidine, m.p. 105°-107° C.

EXAMPLE 27

A mixture of xanthene-9-spiro-4'-piperidine hydrochloride (1 g.), potassium carbonate (1.2 g.) and γ-chloro-p-fluorobutyrophenone ethylene ketal (1.03 g.) in n-butanol is heated under reflux for 48 hours. The mixture is poured into water, extracted with ether, the ether solution evaporated and the residue warmed with 3 N hydrochloric acid for 1 hour to hydrolyse the ketal. The acidic solution is extracted with ethyl acetate, the solvent evaporated and the residue recrystallised from ethyl acetate to give 1'-[3-(p-fluorobenzoyl)propyl]xanthene-9-spiro-4'-piperidine hydrochloride (0.51 g.), m.p. 219°-222° C.

EXAMPLE 28

A mixture of 1'-methylxanthene-9-spiro-4'-piperidine hydrochloride (5 g.), N-chlorosuccinimide (4.5 g.) and dichloromethane (100 ml.) is refluxed for 72 hours. The solution is washed with saturated sodium bicarbonate solution then water and dried with MgSO₄. The solution is evaporated to give a gummy residue which is chromatographed on grade 3 aluminium oxide, Woelm basic. The product is eluted with 30% petroleum-ether (b.p. 60°-80° C.)/chloroform, taken up in ether and the solution treated with ethereal hydrochloric acid. The precipitate is filtered and recrystallised from ethanol-ether to give 2,7-dichloro-1'-methylxanthene-9-spiro-4'-piperidine hydrochloride, m.p. 285° C.

EXAMPLE 29

The following compounds are prepared by repeating the process described in Example 7 using the appropriate dimethanesulphonate and appropriate amine as starting materials:

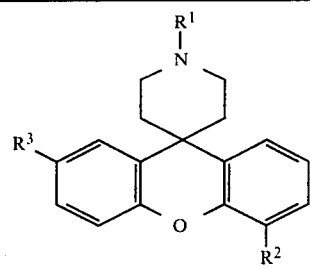

| R¹ | R² | R³ | Salt | m.p.(°C.) | Recrystallisation solvent |
|---|---|---|---|---|---|
| —CH₂—☐ | OCH₃ | Cl | HCl | 245–248 | ethanol-ether |
| —CH₂—△ | OCH₃ | Cl | HCl | 274–277 | ethanol-ether |
| —CH₃ | OCH₃ | Cl | HCl | 248–252 | iso-propanol-ether |
| —CH₂CONH₂ | H | H | HCl | 266 (decomp.) | ethanol-ether |
| —CH₂CH₂N(CH₃)₂ | H | H | 2 HCl·2 H₂O | 265–268 | ethanol |

The 2-chloro-9,9-di-(2-methanesulphonyloxyethyl)-5-methoxyxanthene used as starting material may be prepared as follows:

The second part of Example 2 is repeated using 2-chloro-5-methoxyxanthene as starting material in place of xanthene. The second and third parts of Example 3 are then repeated using the bis-vinyloxyethyl derivative obtained immediately above as starting material. There are thus obtained 9,9-bis-(2-hydroxyethyl)-2-chloro-5-methoxyxanthene, m.p. 192°-195° C. on recrystallisation from toluene and 2-chloro-9,9-di-(2-methanesulphonyloxyethyl)-5-methoxyxanthene, m.p. 165°-167° C. on recrystallisation from toluene-petroleum ether (b.p. 60°-80° C.), respectively.

EXAMPLE 30

One of the demethylation processes described in Example 11 is repeated using the appropriate methoxyxanthene derivative as starting material, and the following compounds are thus obtained:

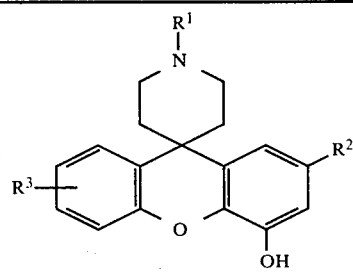

| R¹ | R² | R³ | Method | Salt | m.p.(°C.) | Recrystallisation solvent |
|---|---|---|---|---|---|---|
| —CH₂—△ | H | 7-Cl | B | HCl H₂O | * | |
| —CH₃ | H | 6-Cl | C | HCl ¼ H₂O | 265–267 | ethanol- |

-continued

| R¹ | R² | R³ | Method | Salt | m.p.(°C.) | Recrystallisation solvent |
|---|---|---|---|---|---|---|
| —CH₃ | H | 6-OH | C | HCl ¾ H₂O | 283–284 | ether ethanol-ether |
| —CH₂—☐ | H | 7-Cl | B | HCl ½ H₂O | * | |
| —CH₃ | H | 7-CF₃ | C | HCl ½ H₂O | 188 | ethyl acetate |
| —CH₂CH(OH)CH₃ | H | 7-Cl | B | HCl | * | |
| —CH₃ | H | 6-SCH₃ | B | HCl | 276–277 | ethanol-ether |
| —CH₃ | Cl | H | C | HCl | 268–272 | ethyl acetate-ether |
| —CH₃ | H | 6-F | B | HCl ½ H₂O | 259–260 (decomp.) | ethanol-ether |
| —CH₃ | H | 7-F | C | CHl ½ H₂O | 242–244 | ethyl acetate |
| —CH₃ | H | 8-F | C | HCl | >300 | isopropanol-ether |
| —CH₃ | H | 7-Cl | C | HCl | 181–184 (decomp.) | isopropanol-ether |
| —CH₂CH₂OH | H | H | E | HCl | 248 | ethyl acetate |
| —CH₂CH(OH)CH₃ | H | H | B | HCl H₂O | 199–201 | ethanol-ether |

*non-crystalline glasses-structures confirmed by microanalysis, and by mass spectrometry as follows:

| R¹ | M⊕ | m/e |
|---|---|---|
| —CH₂—CH(CH₂)(CH₂) (cyclopropylmethyl) | 355 | 111 |
| —CH₂—CH(CH₂)(CH₂)—CH₂—CH₂ (cyclobutylmethyl) | 369 | 125 |

-continued

| R¹ | M⊕ | m/e |
|---|---|---|
| —CH₂CH(OH)—CH₃ | 359 | 115 |

EXAMPLE 31

The process described in Example 5 is repeated using an equivalent amount of the appropriate hydroxyxanthene as starting material in place of 4-hydroxy-1'-methylxanthene-9-spiro-4'-piperidine. The following compounds are thus obtained:

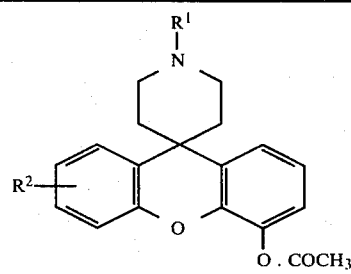

| R¹ | R² | Salt | m.p.(°C.) | Recrystallisation solvent |
|---|---|---|---|---|
| Me | 7-Cl | HCl | * | isopropanol-ether |
| Me | 6-Cl | HCl 2 H₂O | 146–147 | isopropanol-ether |

-continued

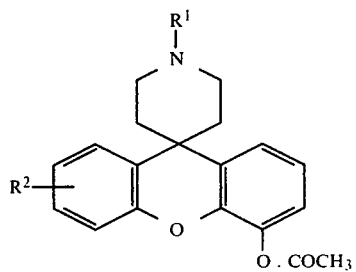

| R¹ | R² | Salt | m.p.(°C.) | Recrystallisation solvent |
|---|---|---|---|---|
| Me | 6-SMe | HCl 1 H₂O | * | ethanol-ether |
| Me | 6-OMe | HCl ½ H₂O | 237–238 (decomp.) | ethyl acetate |
| Me | 6-F | HCl 2 H₂O | 212–214 | ethyl acetate |
| —CH₂—CH(—CH₂—CH₂)—CH₂ | H | HCl ½ H₂O | 244–245 | ethanol-ether |
| —CH₂—CH=C(CH₃)CH₃ | H | HCl 1 H₂O | 202–204 | ethanol-ether |
| Me | 6-OAc | HCl ½ H₂O | 149–151 | ethanol-ether |

*non-crystalline glasses-structures confirmed by microanalysis, and mass spectrometry as follows:

| R¹ | R² | M⊕ |
|---|---|---|
| Me | 7-Cl | 357 |
| Me | 6-SMe | 369 |

The process described in Example 5 is also repeated using an equivalent amount of the appropriate 4-hydroxyxanthene as starting material in place of 4-hydroxy-1'-methylxanthene-9-spiro-4'-piperidine and the appropriate acid chloride in place of acetic anhydride. The following compounds are thus prepared as their hydrochlorides:

| R² | R³ | m.p.(°C.) | Recrystallisation solvent |
|---|---|---|---|
| —CO—CH=CH—C₆H₅ | H | 230–231 | ethyl acetate |
| —CO—CH=CH—C₆H₅ | 6-Cl | 262 | ethanol-ether |
| —CO—CH=CH—C₆H₅ | 7-Cl | ** | ethanol-ether |
| —CO—C₆H₄—Cl | H | 152–155 | isopropanol-ether |
| —SO₂CH₃ | H | 230–235 (decomp.) | ethyl acetate |

EXAMPLE 32

A mixture of 2,5-dichlorobenzoic acid (9.5 g.), 2-methoxyphenol (7.4 g.) and copper bronze (1.0 g.) is added to a solution of sodium methoxide in methanol prepared from sodium (2.53 g.) and methanol (50 ml.). The excess methanol is evaporated and 1,2-dichlorobenzene (50 ml.) is added to the residue. The mixture is stirred and heated under reflux for 2.5 hours. The mixture is cooled, acidified with 3 N hydrochloric acid, filtered to remove copper bronze and extracted with chloroform. The organic layer is separated and extracted with saturated sodium hydrogen carbonate solution. The sodium hydrogen carbonate extract is acidified. The precipitate is filtered off, dissolved in toluene, and the toluene solution treated with carbon, filtered and the solvent evaporated. The solid residue is recrystallised from toluene-petroleum ether (b.p. 60°–80° C.) to give 5-chloro-2-(2'-methoxyphenoxy)benzoic acid, m.p. 115°–118° C.

The above process is repeated using equivalent amounts of the appropriate 2-chlorobenzoic acid in place of 2,5-dichlorobenzoic acid and the appropriate substituted phenol in place of 2-methoxyphenol as starting materials and copper bronze or copper bronze with a trace of cuprous iodide as the catalyst. The following compounds are thus obtained:

| R¹ | R² | R³ | R⁴ | m.p.(°C.) | Recrystallisation solvent |
|---|---|---|---|---|---|
| H | 2'-OMe | 4-Cl | H | * | methanol-water |
| H | 2'-OMe | 5-CF₃ | H | 115–116 | methanol-water |
| H | 2'-OMe | 6-F | H | 147–150 | ethyl acetate-petroleum ether (b.p. 60–80° C.) |
| 4'-Cl | 2'-OMe | H | H | 161–163 | toluene |
| H | H | 4-Cl | 5-Cl | 156–158 | toluene |

-continued

R⁴ position 6, CO₂H position 5', R¹; positions 5,4,3 with R³; 6' position; O linking at 2'; R² at 3',4'

| R¹ | R² | R³ | R⁴ | m.p.(°C.) | Recrystallisation solvent |
|---|---|---|---|---|---|
| H | 2'-OMe | 4-F | H | * | isopropanol |

*Compound characterised by its infra-red spectrum.

EXAMPLE 33

A mixture of 5-chloro-2-(2'-methoxyphenoxy)benzoic acid (15 g.) and polyphosphoric acid (75 g.) is heated on a steam-bath for 3 hours. The mixture is poured into 10 N ammonium hydroxide solution and the precipitate is filtered, dried and recrystallised from toluene to give 3-chloro-5-methoxyxanthone, m.p. 201°–202° C.

The above process is repeated using the appropriate substituted benzoic acid to prepare the following compounds:

Xanthone structure with positions 8,7,6,5 on left ring bearing R³, and 1,2,3,4 on right ring bearing R¹ and R², with C=O bridge and O bridge.

| R¹ | R² | R³ | m.p.(°C.) | Recrystallisation solvent |
|---|---|---|---|---|
| 2-Cl | H | 5-OMe | 194–195 | toluene |
| 2-CF₃ | H | 5-OMe | * | methanol |
| 1-F | H | 5-OMe | 219–220 | toluene |
| 2-Cl | H | 4-OMe | 209–210 | methanol |
| 2-Cl | 3-Cl | H | 174–175 | toluene |
| 3-F | H | 5-OMe | 178 | isopropanol |

*This compound is characterised by its infra-red spectrum.

EXAMPLE 34

A solution of borane-tetrahydrofuran complex in tetrahydrofuran (1 M., 38 ml.) is added slowly to a solution of 3-chloro-5-methoxyxanthone (15 g.) in tetrahydrofuran (200 ml.). The mixture is refluxed for 2 hours, cooled to room temperature and poured into water. The precipitate is filtered, dried and recrystallised from methanol to give 3-chloro-5-methoxyxanthene, m.p. 106°–108° C.

The above process is repeated using the appropriate xanthone to prepare the following compounds:

Xanthene structure with CH₂ bridge and O bridge; positions 8,7,6,5 on left ring with R³; positions 1,2,3,4 on right ring with R¹, R².

| R¹ | R² | R³ | m.p.(°C.) | Recrystallisation solvent |
|---|---|---|---|---|
| 2-Cl | H | 5-OMe | 105–106 | methanol |
| 2-CF₃ | H | 5-OMe | 138–139 | methanol |
| 1-F | H | 5-OMe | 105–107 | methanol |
| 2-Cl | H | 4-OMe | 83–84 | methanol |
| 2-Cl | 3-Cl | H | * | methanol |
| 3-F | H | 5-OMe | * | isopropanol |
| 3-OMe | H | 5-OMe | 135–136 | methanol-water |
| 2-F | H | 5-OMe | ** | methanol |

-continued

| R¹ | R² | R³ | m.p.(°C.) | Recrystallisation solvent |
|---|---|---|---|---|
| 3-SMe | H | 5-OMe | * | methanol |

*This compound is characterised by its infra-red spectrum.
**This compound is characterised by mass spectrometry.

EXAMPLE 35

2-Methoxyphenol (5.0 g.) is added to a stirred mixture of sodium hydride (1.2 g. of a 80% w/w dispersion in mineral oil) and dimethylsulphoxide (50 ml.). When evolution of hydrogen is complete, a solution of the potassium salt of 2-chloro-5-nitro-benzoic acid (5.0 g.) in dimethylsulphoxide (20 ml.) is added and the mixture is stirred and heated on the steam-bath overnight.

The mixture is cooled and poured into excess 3 N hydrochloric acid. The gummy precipitate is extracted with chloroform. The chloroform extract is extracted with saturated sodium hydrogen carbonate solution. Acidification of the sodium hydrogen carbonate extract gives a solid precipitate. This precipitate is recrystallised from methanol-water to give 2-(2'-methoxyphenoxy)-5-nitrobenzoic acid, m.p. 162°–165° C.

The process described in Example 33 is then repeated using the equivalent amount of 2-(2'-methoxyphenoxy)-5-nitrobenzoic acid in place of 4-chloro-2-(2'-methoxyphenoxy)benzoic acid. There is thus obtained 5-methoxy-2-nitroxanthone, m.p. 224°–226° C. on recrystallisation from dimethylformamide.

5-Methoxy-2-nitroxanthone (5.0 g.) is added in small portions during 30 minutes to a stirred mixture of stannous chloride dihydrate (30 g.) and concentrated hydrochloric acid (30 ml.) heated on a steam-bath. The mixture is stirred and heated on a steam-bath for a further 2 hours. The precipitate is filtered off, washed with water and stirred with 5 N sodium hydroxide solution (50 ml.) for 1 hour. The solid is filtered off, made into a slurry with methanol and treated with ethereal hydrochloric acid. The solid is crystallised from methanol-ether to give 2-amino-5-methoxyxanthone hydrochloride, m.p. 271°–273° C.

A solution of sodium nitrite (3.6 g.) in water (100 ml.) is added dropwise with stirring to a mixture of 2-amino-5-methoxyxanthone (10.8 g.), water (160 ml.) and concentrated hydrochloric acid (25 ml.) at 0° C. After the addition is complete the mixture is stirred for a further 10 minutes at 0° C. Urea is added to destroy excess nitrous acid and 40% w/v fluoroboric acid solution (25 ml.) is added and the mixture stirred for 15 minutes at 5° C. The precipitate is filtered off, washed with cold ethanol and ether and air dried to give 5-methoxy-2-xanthonyl diazonium tetrafluoroborate which is used without further purification.

The 5-methoxy-2-xanthonyl diazonium tetrafluoroborate (11.6 g.) is heated at 200° C. for 30 minutes. The residue is chromatographed on silica gel, eluting with chloroform. The solid obtained on evaporation of the solvent is recrystallised from methanol to give 2-fluoro-5-methoxyxanthone, m.p. 170°–172° C.

What we claim is:

1. A compound selected from the group consisting of xanthene derivatives of the formula:

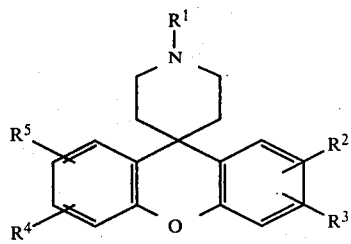

wherein $R^1$ is selected from the group consisting of hydrogen, alkyl of 1 to 4 carbon atoms, alkenyl of 3 to 4 carbon atoms wherein the double bond is separated from the nitrogen atom of the spiropiperidine ring by at least one carbon atom, halo-alkenyl of 3 carbon atoms wherein the double bond is separated from the nitrogen atom of the spiropiperidine ring by a carbon atom, phenylalkyl of 7 to 8 carbon atoms, and hydroxyalkyl of 2 to 3 carbon atoms wherein the oxygen atom is separated from the nitrogen atom of the spiropiperidine ring by at least two carbon atoms, and $R^2$, $R^3$, $R^4$ and $R^5$ are selected from the group consisting of hydrogen, halogen, trifluoromethyl, methoxy, methylthio, hydroxy, acetoxy, cinnamoyloxy and methylsulphinyl, provided that at least two of $R^2$, $R^3$, $R^4$ and $R^5$ stand for hydrogen, or a pharmaceutically-acceptable acid-addition salt thereof.

2. A xanthene derivative as claimed in claim 1 wherein $R^2$ stands for methoxy, hydroxy or acetoxy substituted at the 4-position, $R^4$ stands for fluorine, chlorine, methoxy, methylthio, hydroxy or methylsulphinyl substituted at the 6-position or fluorine or chlorine substituted at the 7- or 8-position, and $R^3$ and $R^5$ stand for hydrogen.

3. An analgesic pharmaceutical composition which comprises as active ingredient an analgesically-effective amount of a xanthene derivative, or a non-toxic pharmaceutically-acceptable acid-addition salt thereof, claimed in claim 1, in association with a major amount of a non-toxic, pharmaceutically-acceptable diluent or carrier.

* * * * *